US010137006B2

(12) United States Patent
Dewey et al.

(10) Patent No.: US 10,137,006 B2
(45) Date of Patent: Nov. 27, 2018

(54) GEARED CAM EXPANDABLE INTERBODY IMPLANT AND METHOD OF IMPLANTING SAME

(71) Applicant: Warsaw Orthopedic, Inc, Warsaw, IN (US)

(72) Inventors: Jonathan M. Dewey, Memphis, TN (US); William D. Armstrong, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 273 days.

(21) Appl. No.: 15/009,582

(22) Filed: Jan. 28, 2016

(65) Prior Publication Data

US 2017/0216045 A1   Aug. 3, 2017

(51) Int. Cl.
  *A61F 2/44*   (2006.01)
  *A61F 2/46*   (2006.01)
  *A61F 2/30*   (2006.01)

(52) U.S. Cl.
  CPC ............ *A61F 2/447* (2013.01); *A61F 2/4611* (2013.01); *A61F 2002/3054* (2013.01); *A61F 2002/30158* (2013.01); *A61F 2002/30411* (2013.01); *A61F 2002/30471* (2013.01); *A61F 2002/30507* (2013.01); *A61F 2002/30523* (2013.01); *A61F 2002/30538* (2013.01); *A61F 2002/30556* (2013.01); *A61F 2002/4475* (2013.01); *A61F 2002/4627* (2013.01); *A61F 2002/4629* (2013.01)

(58) Field of Classification Search
  CPC ....... A61F 2/4455–2/447; A61F 2/4611; A61F 2002/4475
  See application file for complete search history.

(56) References Cited

U.S. PATENT DOCUMENTS

| | | |
|---|---|---|
| 7,850,733 B2 | 12/2010 | Baynham et al. |
| 7,875,078 B2 | 1/2011 | Wysocki et al. |
| 7,909,869 B2 | 3/2011 | Gordon et al. |
| 8,062,375 B2 | 11/2011 | Glerum et al. |
| 8,105,358 B2 | 1/2012 | Phan |
| 8,105,382 B2 | 1/2012 | Olmos et al. |
| 8,123,510 B1 | 2/2012 | Gordon et al. |
| 8,123,810 B2 | 2/2012 | Gordon et al. |
| 8,133,232 B2 | 3/2012 | Levy et al. |
| 8,187,332 B2 | 5/2012 | McLuen |
| 8,382,842 B2 | 2/2013 | Greenhalgh et al. |
| 8,394,145 B2 | 3/2013 | Weiman |
| 8,398,713 B2 | 3/2013 | Weiman |
| 8,403,990 B2 | 3/2013 | Dryer et al. |
| 8,435,298 B2 | 5/2013 | Weiman |
| 8,491,659 B2 | 7/2013 | Weiman |
| 8,518,120 B2 | 8/2013 | Glerum et al. |
| 8,523,944 B2 | 9/2013 | Jimenez et al. |

(Continued)

*Primary Examiner* — Matthew Lawson
*Assistant Examiner* — Amy Sipp

(57) ABSTRACT

A geared cam expandable spinal implant. Rotational motion of a rotating portion is translated into linear motion of a yoke, which moves geared cams at the distal end of the implant to mate with, and walk along, teeth of corresponding racks. The walking of the gear cam teeth along the rack teeth creates a regular rate of implant expansion, reduces initial excessive expansion force applied to the implant, and provides fine adjustment of the expansion rate and force.

23 Claims, 27 Drawing Sheets

(56) References Cited

U.S. PATENT DOCUMENTS

| | | |
|---|---|---|
| 8,556,979 B2 | 10/2013 | Glerum et al. |
| 8,568,481 B2 | 10/2013 | Olmos et al. |
| 8,628,577 B1 | 1/2014 | Jimenez |
| 8,628,578 B2 | 1/2014 | Miller et al. |
| 8,632,595 B2 | 1/2014 | Weiman |
| 8,663,329 B2 | 3/2014 | Ernst |
| 8,679,183 B2 | 3/2014 | Glerum et al. |
| 8,685,098 B2 | 4/2014 | Glerum et al. |
| 8,709,086 B2 | 4/2014 | Glerum |
| 8,778,025 B2 | 7/2014 | Ragab et al. |
| 8,795,366 B2 | 8/2014 | Varela |
| 8,888,853 B2 | 11/2014 | Glerum et al. |
| 8,888,854 B2 | 11/2014 | Glerum et al. |
| 8,894,711 B2 | 11/2014 | Varela |
| 8,894,712 B2 | 11/2014 | Varela |
| 8,926,704 B2 | 1/2015 | Gerum et al. |
| 8,940,049 B1 | 1/2015 | Jimenez et al. |
| 9,039,771 B2 | 5/2015 | Glerum et al. |
| 9,119,730 B2 | 9/2015 | Glerum et al. |
| 9,801,640 B2* | 10/2017 | O'Neil .............. A61B 17/1671 |
| 2003/0236520 A1* | 12/2003 | Lim .................... A61B 17/025 606/99 |
| 2004/0193158 A1* | 9/2004 | Lim .................... A61B 17/025 606/99 |
| 2011/0054621 A1 | 3/2011 | Lim |
| 2011/0172721 A1 | 7/2011 | Frigg et al. |
| 2011/0172774 A1 | 7/2011 | Varela |
| 2012/0035729 A1 | 2/2012 | Glerum et al. |
| 2012/0109319 A1 | 5/2012 | Perisic |
| 2012/0150304 A1 | 6/2012 | Glerum et al. |
| 2012/0150305 A1 | 6/2012 | Glerum et al. |
| 2012/0158146 A1 | 6/2012 | Glerum et al. |
| 2012/0158147 A1 | 6/2012 | Glerum et al. |
| 2012/0158148 A1 | 6/2012 | Glerum et al. |
| 2013/0144388 A1 | 6/2013 | Emery et al. |
| 2013/0158664 A1* | 6/2013 | Palmatier ............... A61F 2/447 623/17.16 |
| 2013/0190876 A1* | 7/2013 | Drochner ............... A61F 2/442 623/17.16 |
| 2013/0197642 A1* | 8/2013 | Ernst ..................... A61F 2/442 623/17.16 |
| 2014/0121774 A1 | 5/2014 | Glerum et al. |
| 2014/0194991 A1* | 7/2014 | Jimenez ................ A61F 2/442 623/17.15 |
| 2014/0324171 A1 | 10/2014 | Glerum et al. |
| 2014/0343678 A1* | 11/2014 | Suddaby ................. A61F 2/46 623/17.16 |
| 2015/0272743 A1* | 10/2015 | Jimenez ................ A61F 2/447 623/17.16 |
| 2016/0166396 A1* | 6/2016 | McClintock ....... A61F 2/30771 623/17.16 |
| 2016/0331542 A1* | 11/2016 | Faulhaber ............. A61F 2/447 |
| 2017/0231778 A1* | 8/2017 | Overes ................. A61F 2/4425 623/17.16 |

* cited by examiner

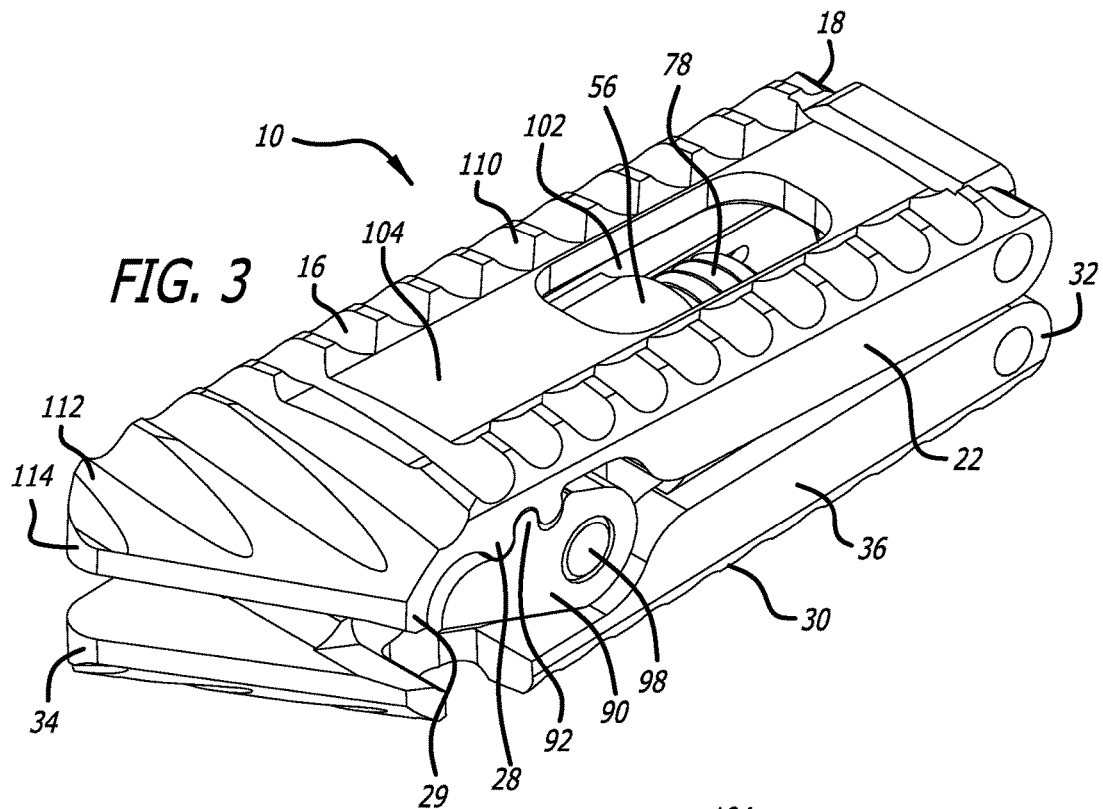
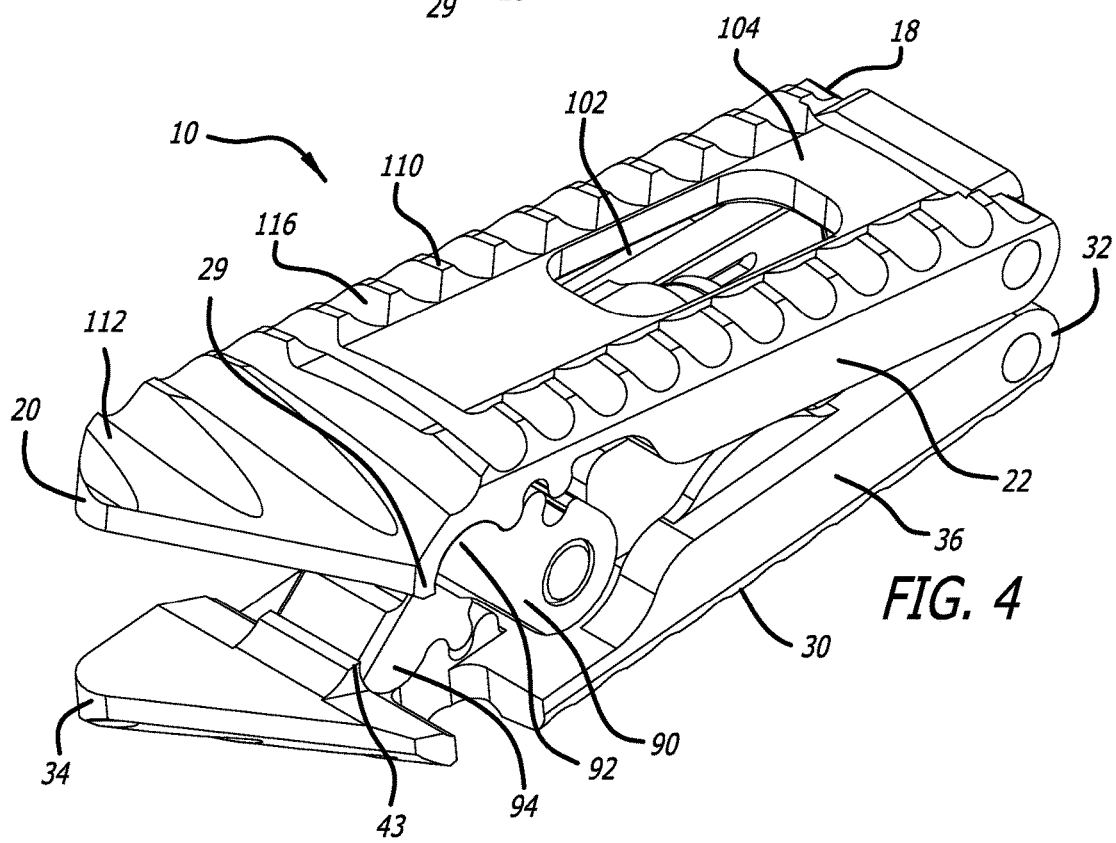

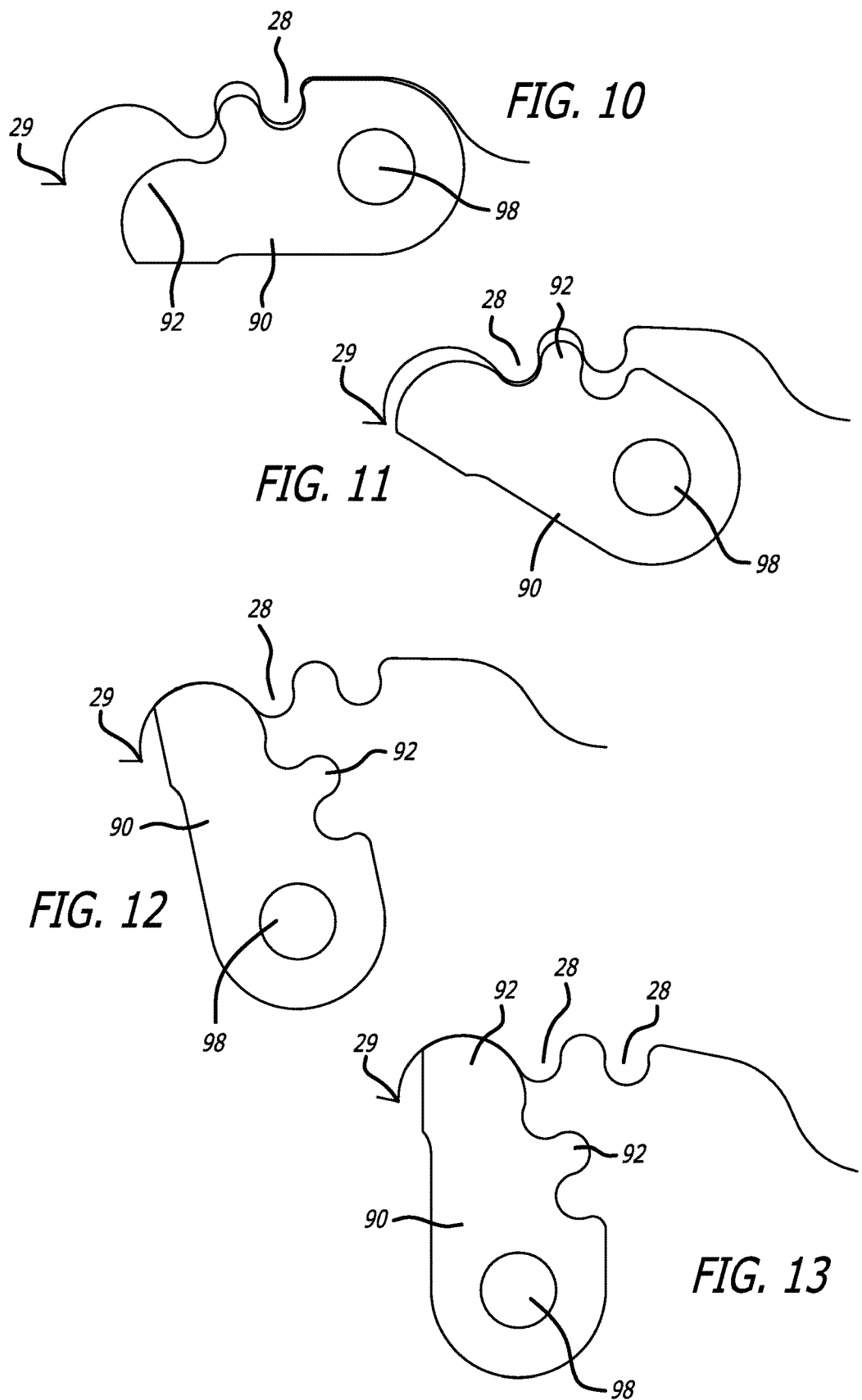

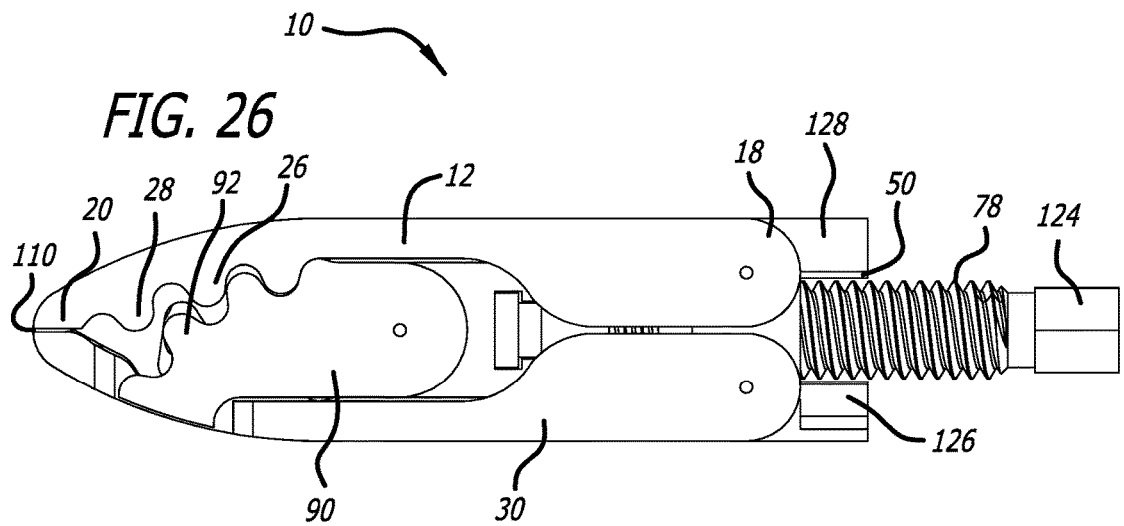
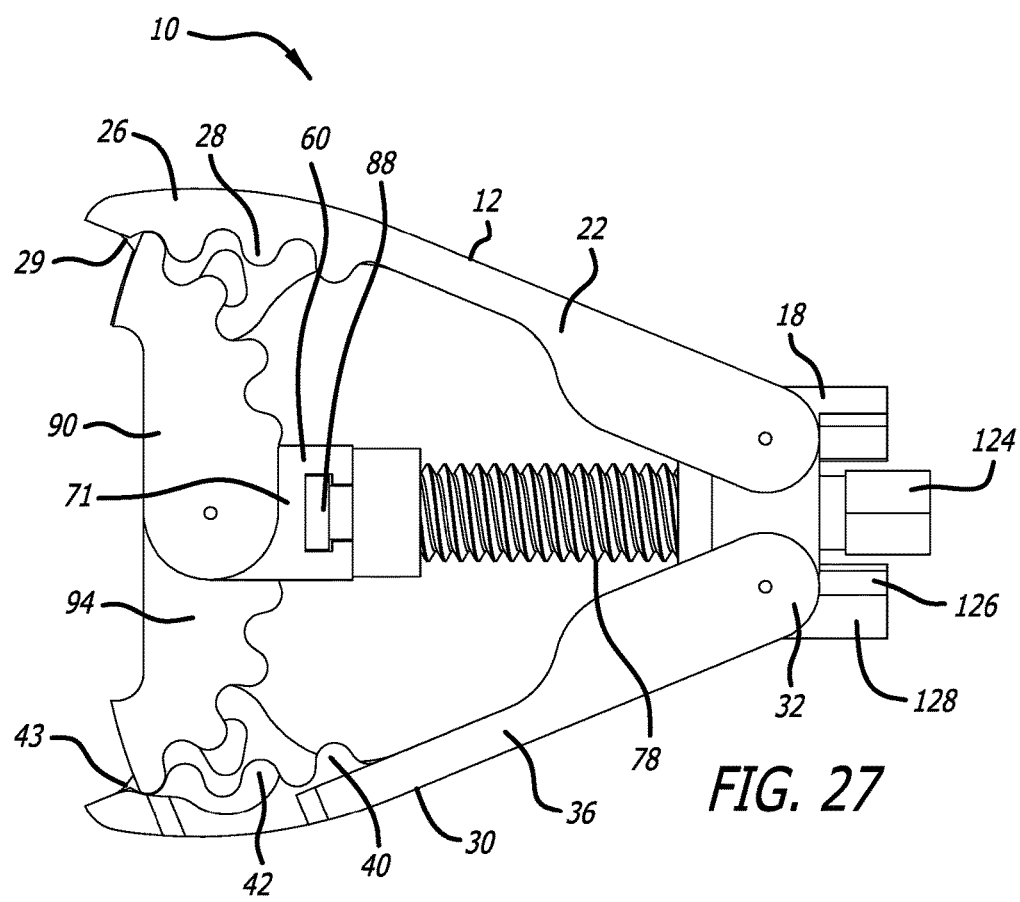

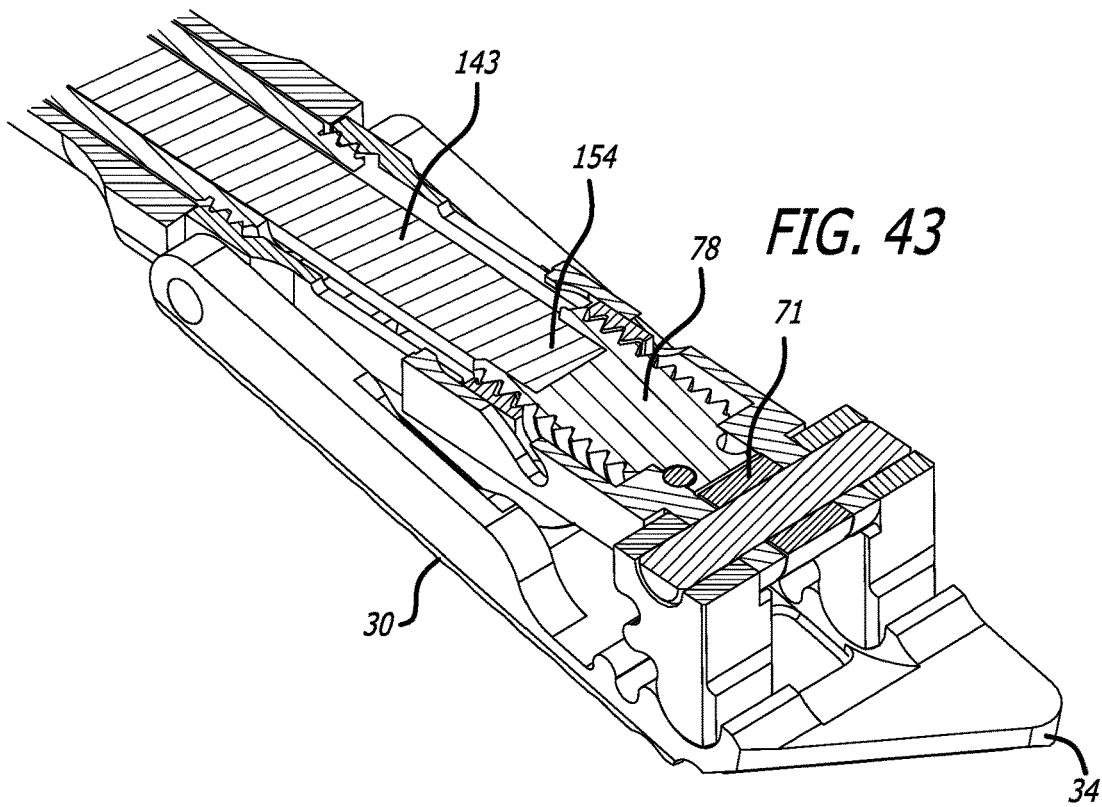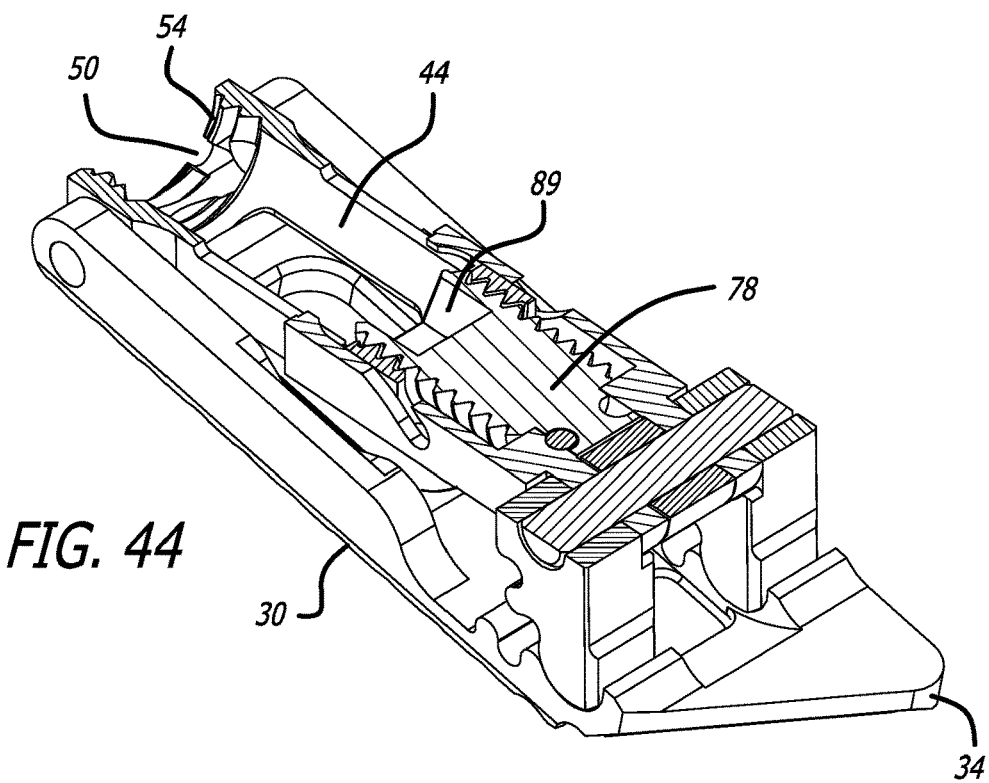

GEARED CAM EXPANDABLE INTERBODY IMPLANT AND METHOD OF IMPLANTING SAME

FIELD OF THE INVENTION

The present invention relates to a spinal implant, and a method for implanting the implant in a patient's disc space between two adjacent vertebral bodies. More particularly, the present invention relates to an expandable spinal implant including geared cams, configured to expand within the patient's disc space, from a collapsed position to an expanded position.

DESCRIPTION OF THE RELATED ART

Expandable spinal implants are known. Existing expandable spinal implants use conventional "4-bar" and "crank slider" expansion mechanisms. Following insertion, while in the collapsed position, into a surgically-enhanced disc space, the existing expandable spinal implants are expanded. The existing expandable implants have been known at least to (1) apply an undesireable excessive initial expansion force to the disc space, (2) apply an irregular expansion force to the disc space, and (3) lack a reliable capability for fine adjustment. Existing expandable implants also lack different configurations at the distal tip of the implant, which often could be advantageous, e.g., to ensure engagement between the distal tip and the adjacent vertebral bodies.

SUMMARY OF THE INVENTION

It is an object of the present invention to provide an expandable spinal implant which obviates one or more of the shortcomings of the related art.

It is another object of the present invention to provide an expandable spinal implant for insertion into a patient's disc space between an upper vertebral body and a lower vertebral body. The implant has a proximal end and a distal end defining a mid-longitudinal axis therebetween, and is expandable between a collapsed position, a partially-expanded position, and a fully-expanded position.

The implant includes an upper endplate. The upper endplate has a proximal end, a distal end, an outer surface, at least one side surface, and an inner surface. A portion of the inner surface includes an upper rack portion. The upper rack portion includes downwardly-projecting teeth intermediate the proximal end and the distal end of the upper endplate, and at least one distal-most downwardly-projecting tooth proximate the distal end of the upper endplate. The implant further includes a lower endplate. The lower endplate has a proximal end, a distal end, an outer surface, at least one side surface, and an inner surface. A portion of the inner surface includes a lower rack portion. The lower rack portion includes upwardly-projecting teeth intermediate the proximal end and the distal end of the lower endplate, and at least one distal-most upwardly-projecting tooth proximate the distal end of the lower endplate. The proximal end of the lower endplate is pivotally connected to the proximal end of the upper endplate.

A chassis portion is mounted within the implant between the upper endplate and the lower endplate. The chassis portion has a proximal end and a distal end. The proximal end has an opening defined therein.

A yoke is movably mounted within the chassis portion. The yoke has a proximal end and a distal end. The yoke is defined by first and second parallel spaced-apart walls extending from the proximal end to the distal end. A distal cross-piece, transverse to the longitudinal axis, connects the distal ends of the first and second walls of the yoke.

A rotating portion is rotatably mounted within the chassis portion. The rotating portion has a proximal end and a distal end. The distal end is configured to contact the distal cross-piece of the yoke. The proximal end has an opening defined therein, configured to receive a distal end of an implant expansion tool.

At least one first spur gear is rotatably mounted on a distal end of one of the first and second walls of the yoke. The at least one first spur gear has teeth configured to engage the downwardly-projecting teeth of the upper rack portion. At least one second spur gear is rotatably mounted on a distal end of one of the first and second walls of the yoke. The at least one second spur gear has teeth configured to engage the upwardly-projecting teeth of the lower rack portion.

The rotating portion is configured to translate rotational motion thereof to linear motion of the yoke. The yoke translates the linear motion to rotation of the spur gears with respect to the yoke, causing the spur gears to walk along the upper rack gear teeth and lower rack gear teeth, respectively, toward the distal end of the implant, thereby moving the implant through the partially-expanded position. When the spur gear teeth abut against the distal-most teeth, respectively of the upper rack or the lower rack, the implant has reached the fully-expanded position.

It is a further object of the present invention to provide a method of implanting the expandable spinal implant described above into a patient's disc space between an upper vertebral body and a lower vertebral body. The method includes inserting the implant into a surgically-prepared disc space, in the collapsed position, using an implant insertion tool, rotating the rotating portion, defining a rotational motion, translating the rotational motion of the rotating portion into a linear motion of the yoke toward the distal end of the implant, rotating the spur gears with respect to the yoke, thereby walking the spur gears along the projecting teeth of the respective upper and lower racks, and expanding the implant through the partially-expanded position to the fully-expanded position. The insertion tool includes an outer hollow shaft, an inner hollow shaft configured to pass through the outer shaft, and an elongated driver configured to pass through the inner hollow shaft. The elongated driver has a blunt distal end configured to contact a portion of the implant. Application of a movement to the elongated driver is transferred to the implant, forcing the implant into the disc space. After removal of the elongated driver, bone growth material can be routed through the inner shaft and into the implant.

These and other objects of the present invention will be apparent from review of the following specification and the accompanying drawings.

BRIEF DESCRIPTION OF THE DRAWINGS

FIG. 3 is an upper perspective view of a geared cam expandable spinal implant in accordance with the invention, in a partially expanded position;

FIG. 4 is an upper perspective view of a geared cam expandable spinal implant in accordance with the invention, in a fully expanded position;

FIGS. 10-16 are side schematic views of a multi-stage expansion mechanism used in one preferred embodiment of a geared cam expandable spinal implant in accordance with the invention;

FIG. 26 is a side cross-sectional view of a geared cam expandable spinal implant in accordance with the invention, in a collapsed position;

FIG. 27 is a side cross-sectional view of a geared cam expandable spinal implant in accordance with the invention in a fully expanded position;

FIG. 43 is an upper perspective cross sectional view of a geared cam expandable implant in accordance with the invention being inserted into a disc space by an implant insertion tool in accordance with the invention;

FIG. 44 is an upper perspective cross sectional view of a geared cam expandable implant inserted into the disc space, following removal of the implant insertion tool;

DETAILED DESCRIPTION OF THE PREFERRED EMBODIMENTS

A geared cam expandable spinal implant 10 is configured to be inserted in a surgically-enhanced disc space between an upper vertebral body and an adjacent lower vertebral body. The implant 10 includes a proximal end 12 and a distal end 14, defining a mid-longitudinal axis L-L therebetween.

Figure 6:
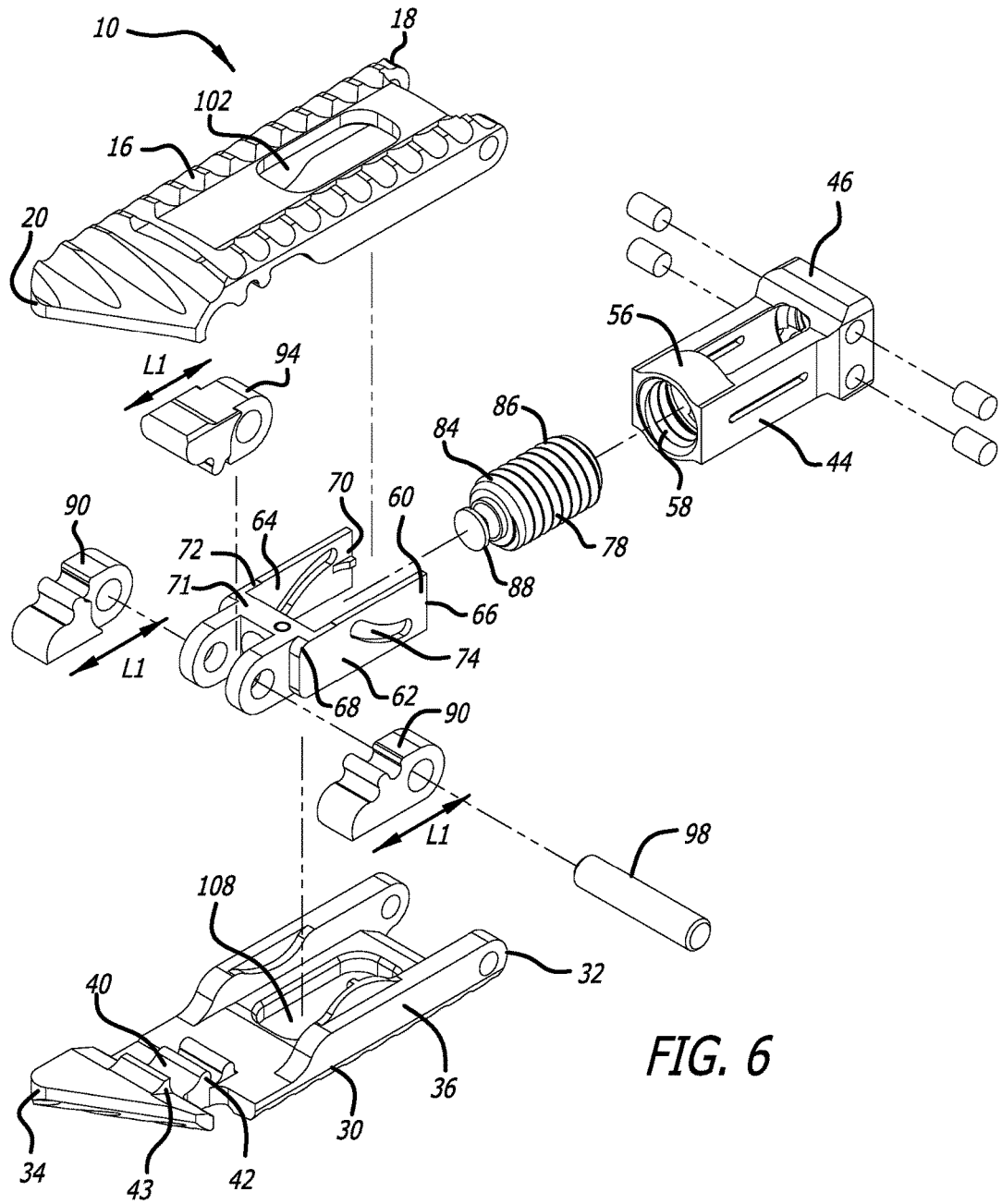
FIG. 6 is an exploded parts view of a geared cam expandable spinal implant in accordance with the invention.
Figure 7:
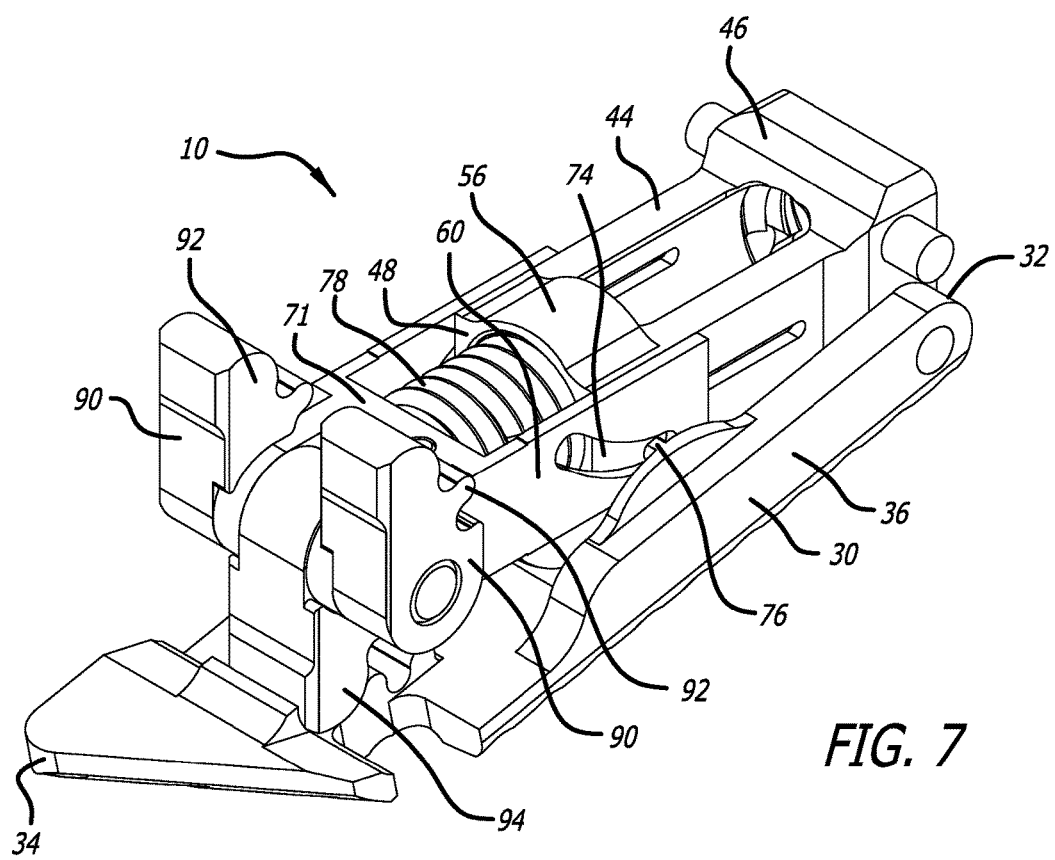
FIG. 7 is an upper perspective view of a lower endplate, chassis portion, yoke, rotating portion, and spur gears, of a geared cam expandable spinal implant in accordance with the invention.
Figure 8:
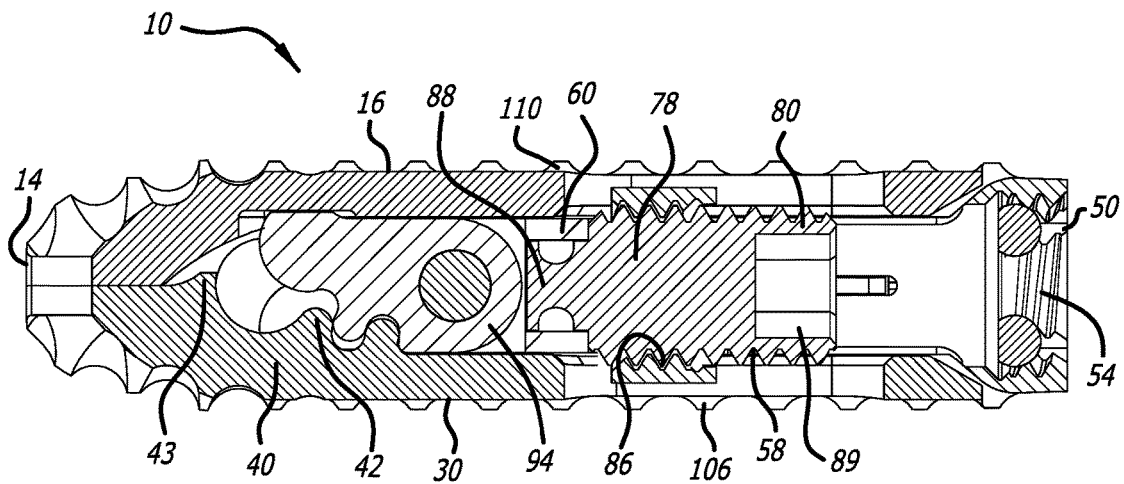
FIG. 8 is a cross-sectional side view of a geared cam expandable spinal implant in accordance with the invention, in a collapsed position.
Figure 9:
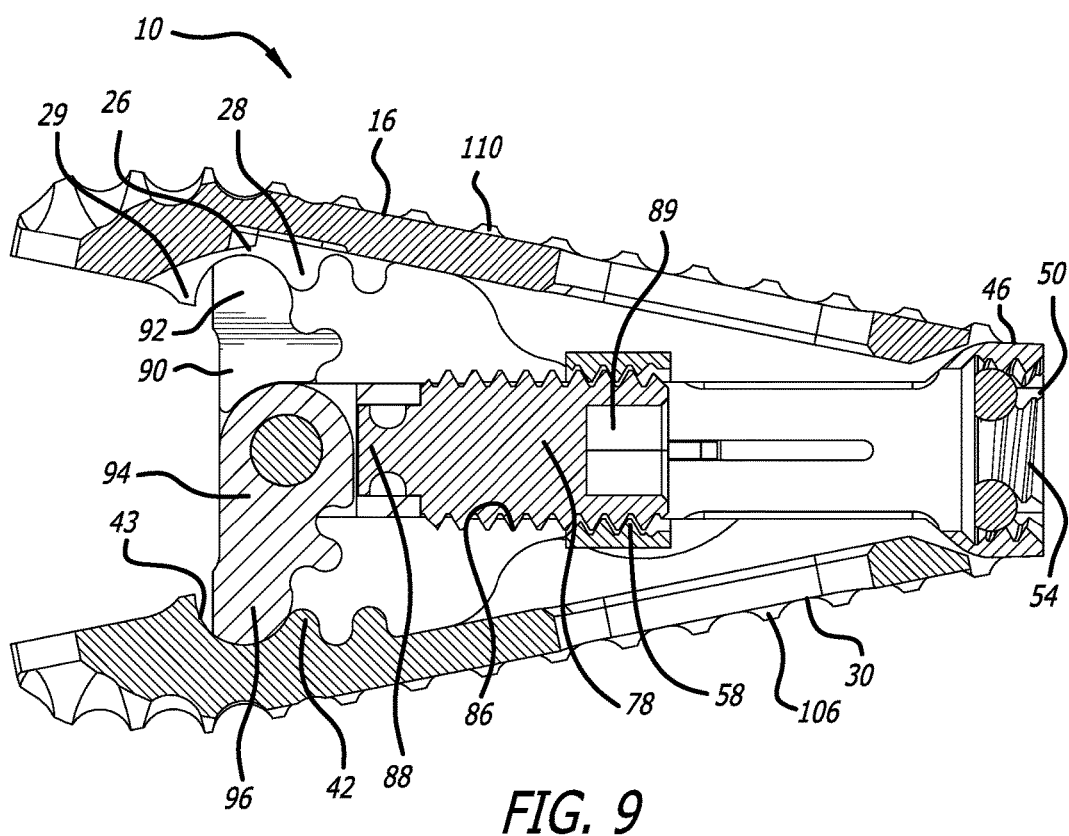
FIG. 9 is a cross-sectional side view of a geared cam expandable spinal implant in accordance with the invention, in a fully-expanded position.

In one embodiment, the implant 10 includes an upper endplate 16. As depicted in FIGS. 6, 8, and 9, the upper endplate 16 includes a proximal end 18, a distal end 20, side surfaces 22, and an inner surface 24. The inner surface 24 includes an upper rack portion 26, which includes downwardly-projecting teeth 28, and a distal-most downwardly-projecting tooth 29.

In one embodiment, the implant 10 includes a lower endplate 30. The lower endplate 30 includes a proximal end 32, a distal end 34, side surfaces 36, and an inner surface 38.

The inner surface 38 includes a lower rack portion 40, which includes upwardly-projecting teeth 42, and a distal-most upwardly-projecting tooth 43.

In one embodiment, the implant 10 includes a chassis portion 44 mounted within the implant between the upper endplate 16 and the lower endplate 30. The chassis portion 44 includes a proximal end 46 and a distal end 48. As depicted in FIGS. 7-9, 21, 22, and 46, the proximal end 46 of the chassis portion 44 is a wall perpendicular to the mid-longitudinal axis L-L, having an opening 50 defined through the wall, and one or more depressions 52 defined in the wall proximate the opening 50. The chassis portion 44 further includes a first set of internal threads 54 defined in the opening 50 of the proximal end 46.

In one embodiment, as depicted in FIGS. 1-7, the chassis portion 44 includes an arcuate portion 56 intermediate the proximal end 46 and the distal end 48. A second set of internal threads 58 are defined on an inner surface of the arcuate portion 56.

Figure 5:
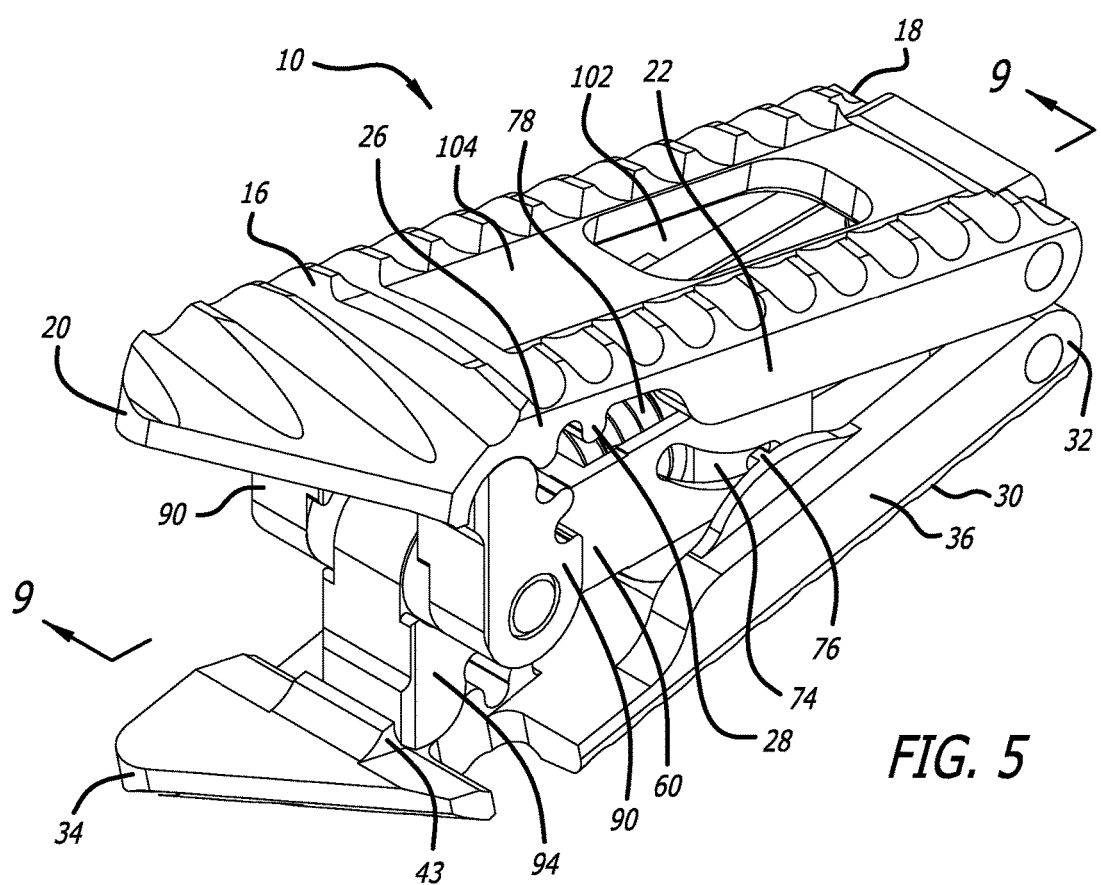
FIG. 5 is an upper perspective view of a geared cam expandable spinal implant in accordance with the invention, in a fully expanded position.

In one embodiment, a yoke 60 is movably mounted within the chassis portion 44. The yoke 60 is defined by a first wall 62, and a parallel second wall 64 spaced away from the first wall 62. First wall 62 has a proximal end 66 and a distal end 68. Second wall 64 has a proximal end 70 and a distal end 72. As depicted in FIGS. 6, 7, and 41-43, distal ends 68 and 72 of first and second walls 62 and 64 can be connected by a distal end cross-piece 71. As depicted in FIG. 5, the yoke 60 includes a slot 74 defined in at least one of first wall 62 and second wall 64. Each slot 74 is configured to receive therein a pin 76 projecting from an inner side surface of the lower endplate 30. Insertion of the pin 76 into the slot 74 assists in preventing separation of the implant 10.

In one embodiment, a rotating portion 78 is rotatably mounted within the chassis portion 44. Rotating portion 78 includes a proximal end 80, a distal end 82, and an outer surface 84, with outer threads 86 defined on the outer surface 84. In one embodiment, as depicted in FIGS. 6, 8, 9, 20-22, 25-27, 30, and 31, the distal end 82 includes a T-shaped projection 88. The invention, however, is not limited to having a T-shaped projection at the distal end 82 of the rotating portion 78. In one embodiment, the proximal end 80 of the rotating portion includes an opening 89, configured to receive therein a distal end of an implant expansion tool (not shown). The invention is not limited to any particular configuration for the opening 89, as long as the rotating portion 78 can be rotated by the implant expansion tool. As depicted in FIGS. 8 and 9, the opening 89 has a polygonal shape to receive a polygonal-shaped distal end of the implant expansion tool. As another example, but not by way of limitation, the opening 89 could be threaded to receive a threaded distal end of the implant expansion tool.

Figure 47:
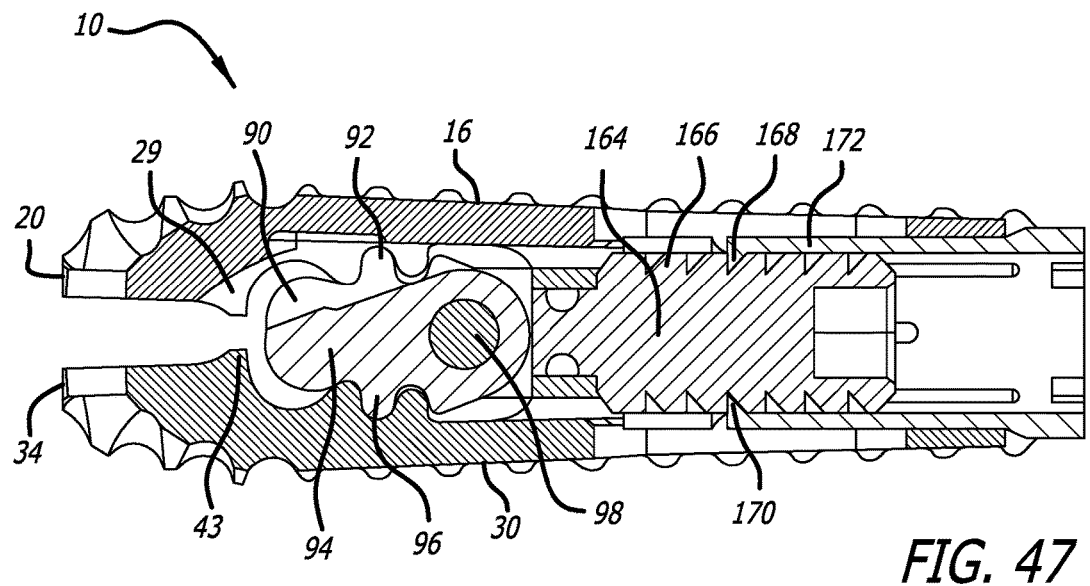
FIG. 47 is a side cross-sectional view of a geared cam expandable spinal implant in accordance with the invention.
Figure 48:
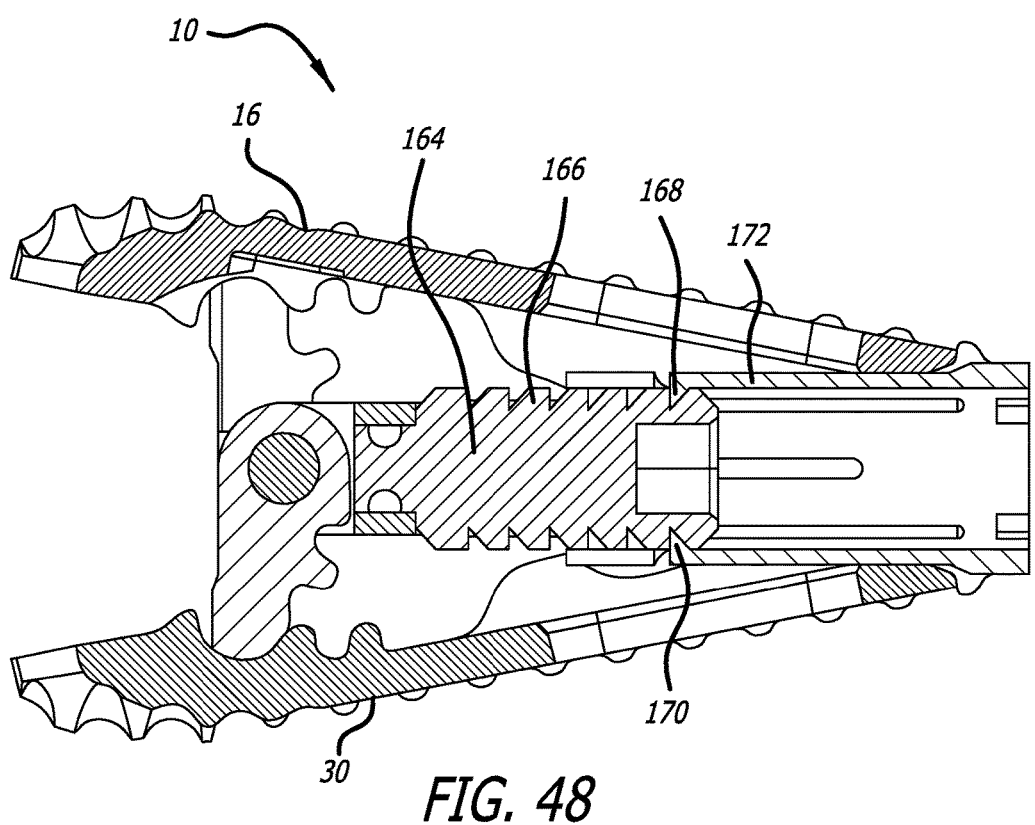
FIG. 48 is a side cross-sectional view of a geared cam expandable spinal implant in accordance with the invention.
Figure 49:
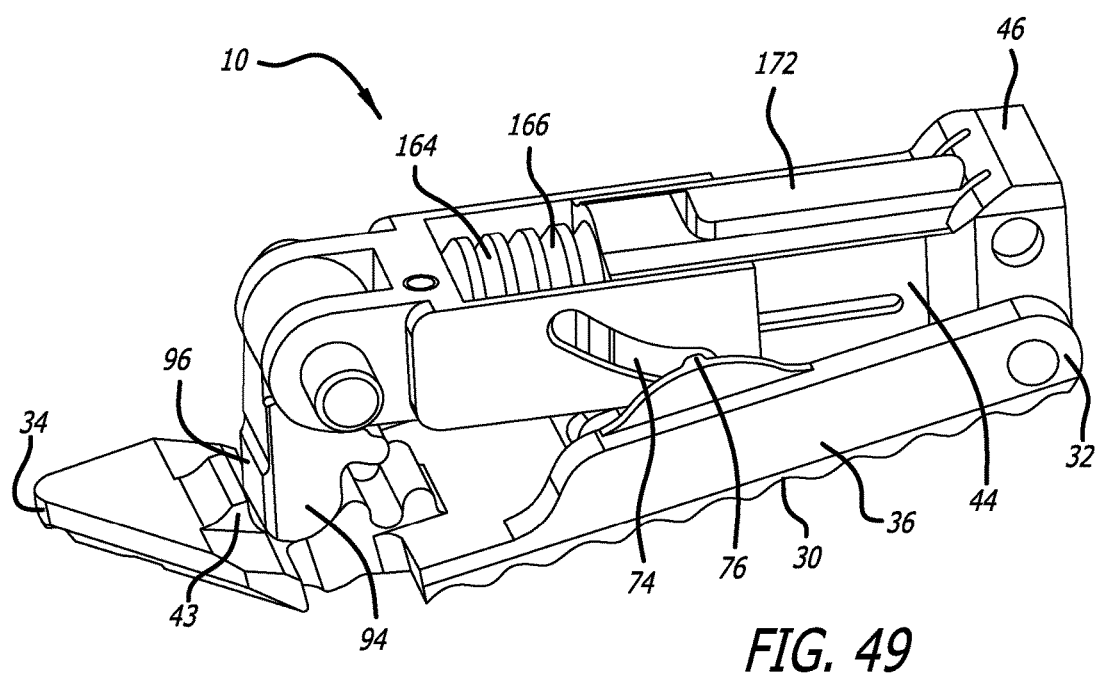
FIG. 49 is a partial upper perspective view depicting a lower endplate, chassis, yoke, lower spur gear, and cylinder with circumferential ratchet teeth.

In one embodiment, as depicted in FIG. 47-49, the threaded rotating portion 78 has been replaced by a cylinder 164 with circumferential ratchet teeth 166, and the mating threads 54 on the arcuate portion 56 have been replaced by integral pawls 168. The ratchet teeth 166 are separated by grooves 170 The pawls 168 are allowed to flex because they are integral with "live" springs 172 attached to the chassis portion 44. In this embodiment, as the ribbed cylinder 164 is advanced, each pawl 168 advances to the next respective groove 170. In this manner, the distal end of the cylinder 164 pushes on the yoke 60, causing the spur gears 90 and 94 to walk toward the distal end 14 of the implant 10, expanding the implant, while the pawls 168 are retained in the respective grooves 170 between the ratchet teeth 166, thereby retaining the implant 10 in its current expanded position.

In one embodiment, a pair of first spur gears 90 is rotatably mounted to the distal end 68 of the first wall 62 of the yoke 60, and the distal end 72 of the second wall 64 of the yoke 60, respectively. Each first spur gear 90 includes projecting first spur gear teeth 92, configured to engage with the downwardly-projecting teeth 28 of the upper rack portion 26.

Figure 20:
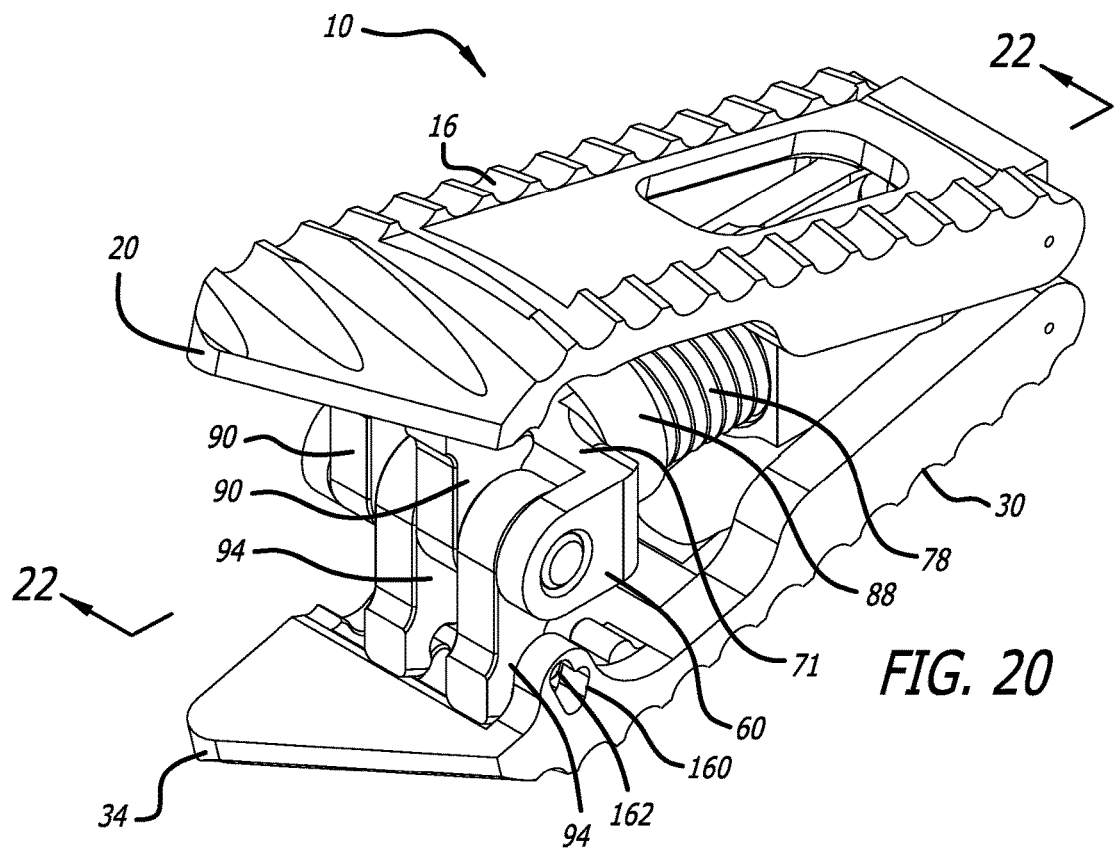
FIG. 20 is an upper perspective view of a geared cam expandable spinal implant in accordance with the invention, in a fully expanded position.
Figure 21:
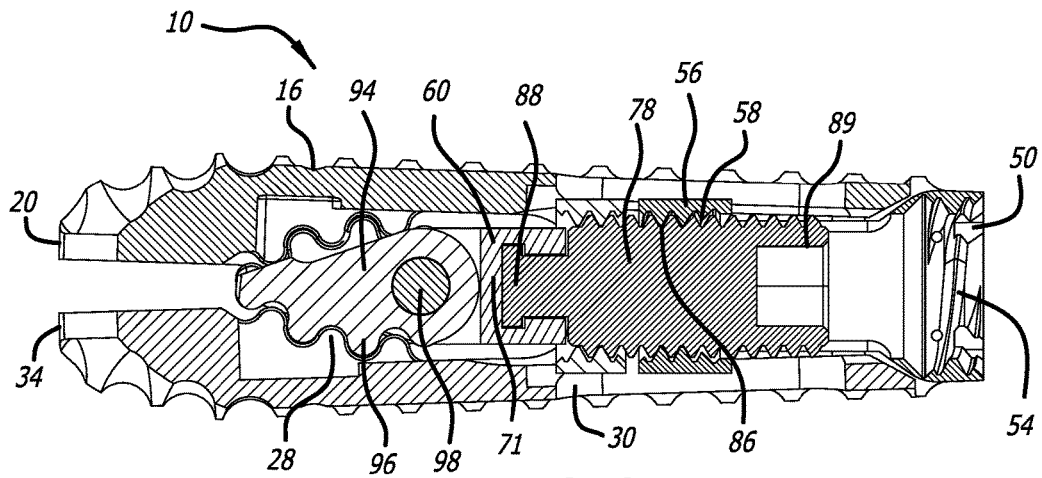
FIG. 21 is a side cross-sectional view of a geared cam expandable spinal implant in accordance with the invention, in a partially expanded position.
Figure 22:
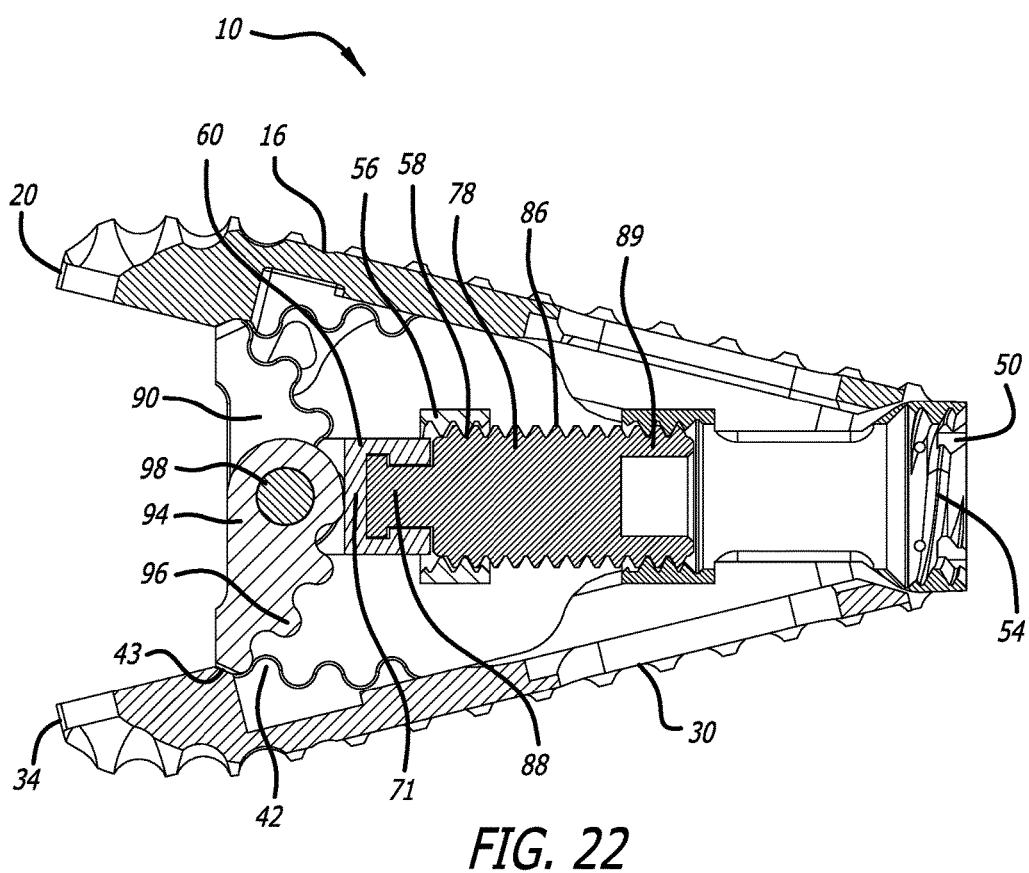
FIG. 22 is a side cross-sectional view of a geared cam expandable spinal implant in accordance with the invention, in a fully expanded position.

In one embodiment, as depicted in FIGS. 5-7, 18, 24, 36, and 37, a second spur gear 94 is rotatably mounted between the distal end 68 of the first wall 62 of the yoke 60, and the distal end 72 of the second wall 64 of the yoke 60, respectively. As depicted in FIG. 6, the spur gears 90 and 94 are rotatably attached to the yoke 60 with a pin 98. The second spur gear 94 includes projecting second spur gear teeth 96, configured to engage with the upwardly-projecting teeth 42 of the lower rack portion 40. The invention is not limited to having two first spur gears 90 and one second spur gear 96. For example, as depicted in FIG. 20, the invention can include two first spur gears 90 and two second spur gears 96. It is also within the scope of the invention to have one first spur gear 90, and two second spur gears 96.

Figure 19:
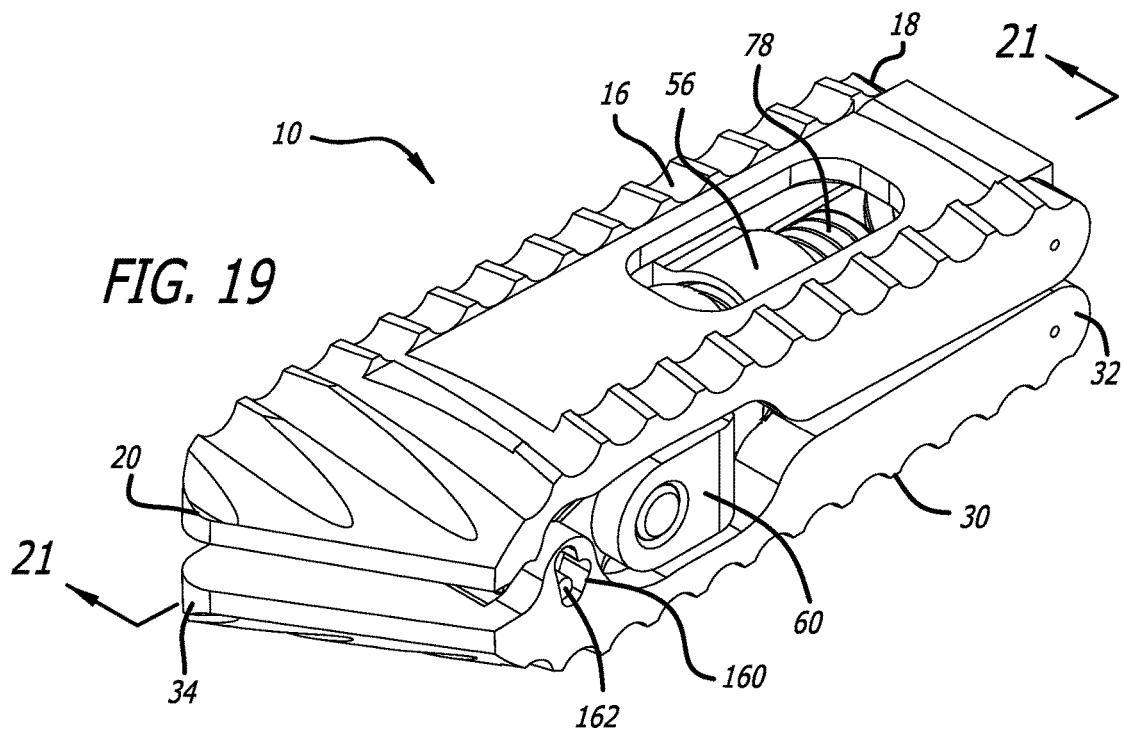
FIG. 19 is an upper perspective view of a geared cam expandable spinal implant in accordance with the invention, in a partially expanded position.

In one embodiment, as depicted in FIGS. 19 and 20, a slot 160 is defined in the side surface 36 proximate the distal end 34 of the lower endplate 30, and a pin 162 is defined projecting from a second spur gear 96. Pin 162 is configured to engage with slot 160, to help prevent the upper and lower endplates from separating.

In one embodiment, the rotating portion 78 rotates within the chassis portion 44, with the outer threads 86 of the rotating portion 78 engaging threaded portion 58 of the chassis portion 44, until the distal end 82 of the rotating portion 78 contacts the distal cross-piece 71 of the yoke 60. Rotation of the rotating portion 78 is translated into linear motion of the yoke 60 towards the distal end 14 of the implant 10. Linear motion of the yoke 60 causes the first spur gears 90, and the second spur gears 94 to rotate. The respective first spur gear teeth 92 and second spur gear teeth 96 "walk" towards the distal end 14 of the implant 10 in the respective downwardly-projecting teeth 28 of the upper rack portion 26, and upwardly-projecting teeth 42 of the lower rack portion 40. As the teeth "walk," the upper endplate 16 is moved away from the lower endplate 30, thereby moving the implant 10 into and through the partially-expanded position. When the respective spur gear teeth 92 and 96 reach the respective distal-most downwardly-projecting tooth 29, or alternately the distal-most upwardly-projecting tooth 43, they can "walk" no farther towards the distal end of the implant 10, and the implant has reached the fully-expanded position. The amount of expansion in the fully-expanded position is related to the length of the spur gears. As depicted in FIG. 6, the spur gears have a length S1, but different spur gear lengths are possible, depending on the requirements of an individual patient. Different amounts of full-expansion, related to spur gear length are depicted, for example, in FIGS. 4, 5, 9, 20, and 22.

Figure 32:
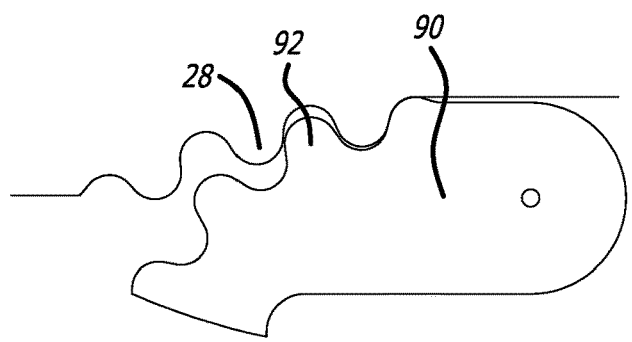
FIGS. 32-34 are side schematic views of a spur gear and rack in a one-stage expansion mechanism.
Figure 33:
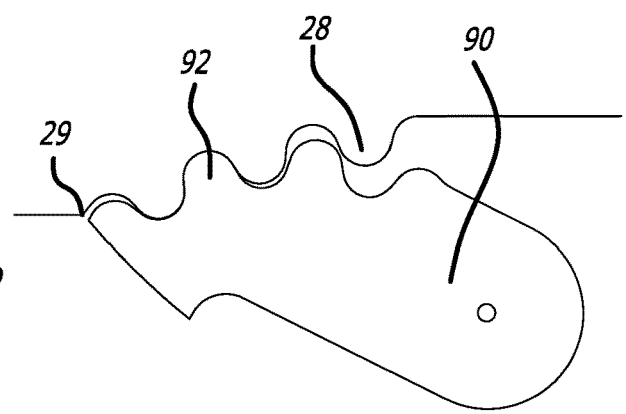
Figure 34:
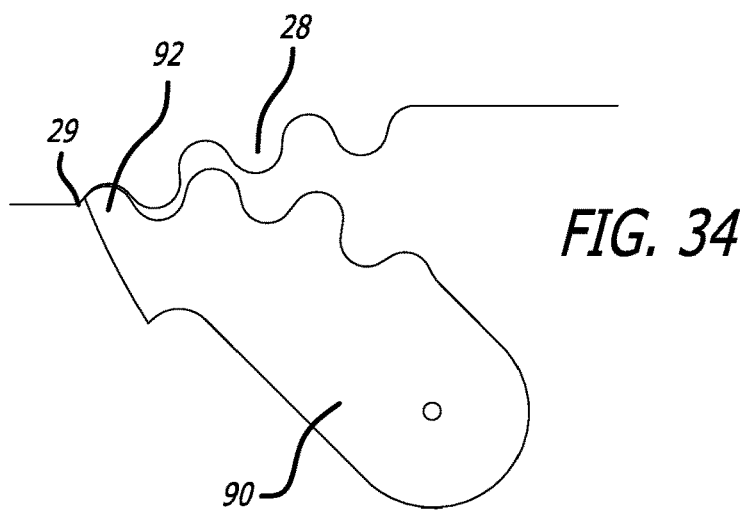

In one embodiment, as depicted in FIGS. 32-34, the spur gears 92 and 94 "walk" along the respective racks 26 and 40 in a one-stage expansion movement, with the respective spur simply rolling along the respective rack.

Figure 14:
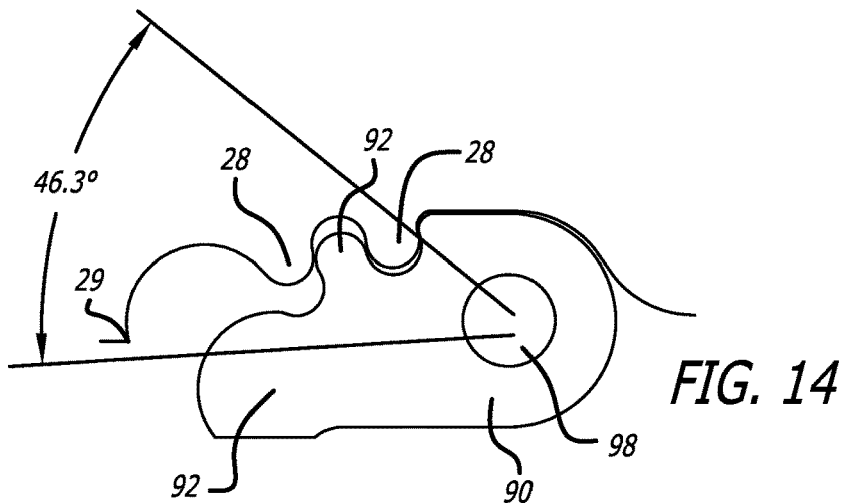
Figure 15:
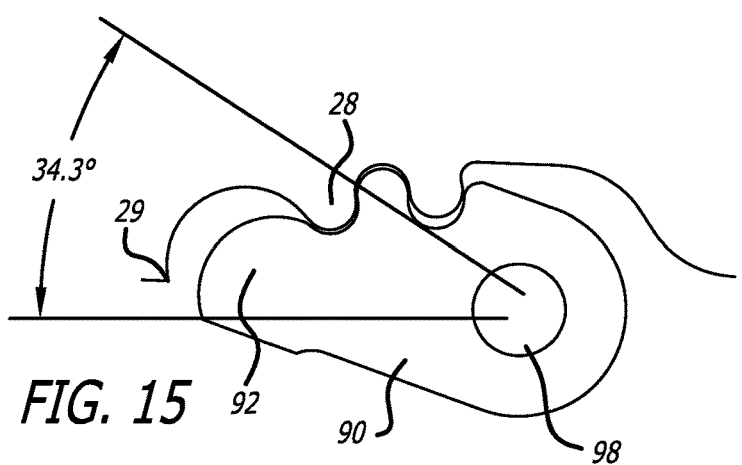
Figure 16:
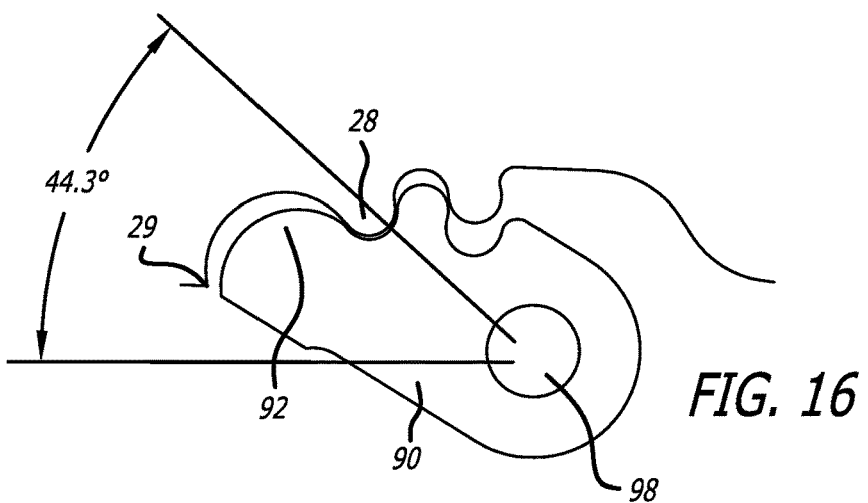
Figure 17:
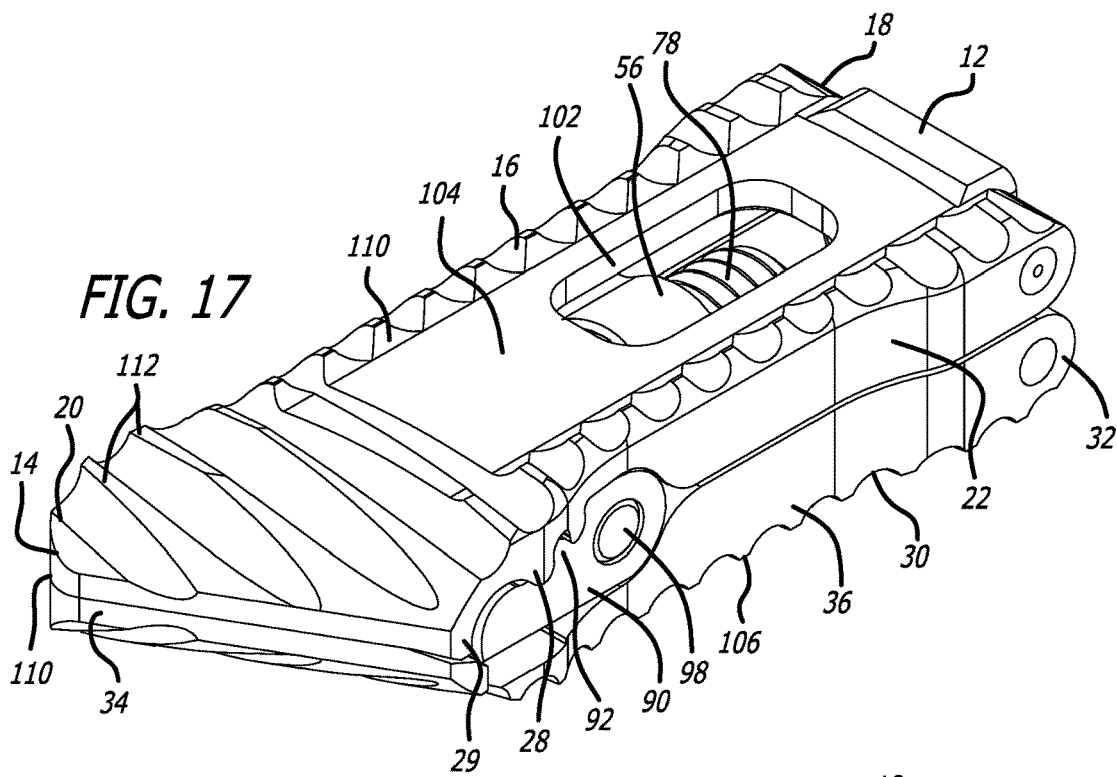
FIG. 17 is an upper perspective view of a geared cam expandable spinal implant in accordance with the invention, in a collapsed position.
Figure 18:
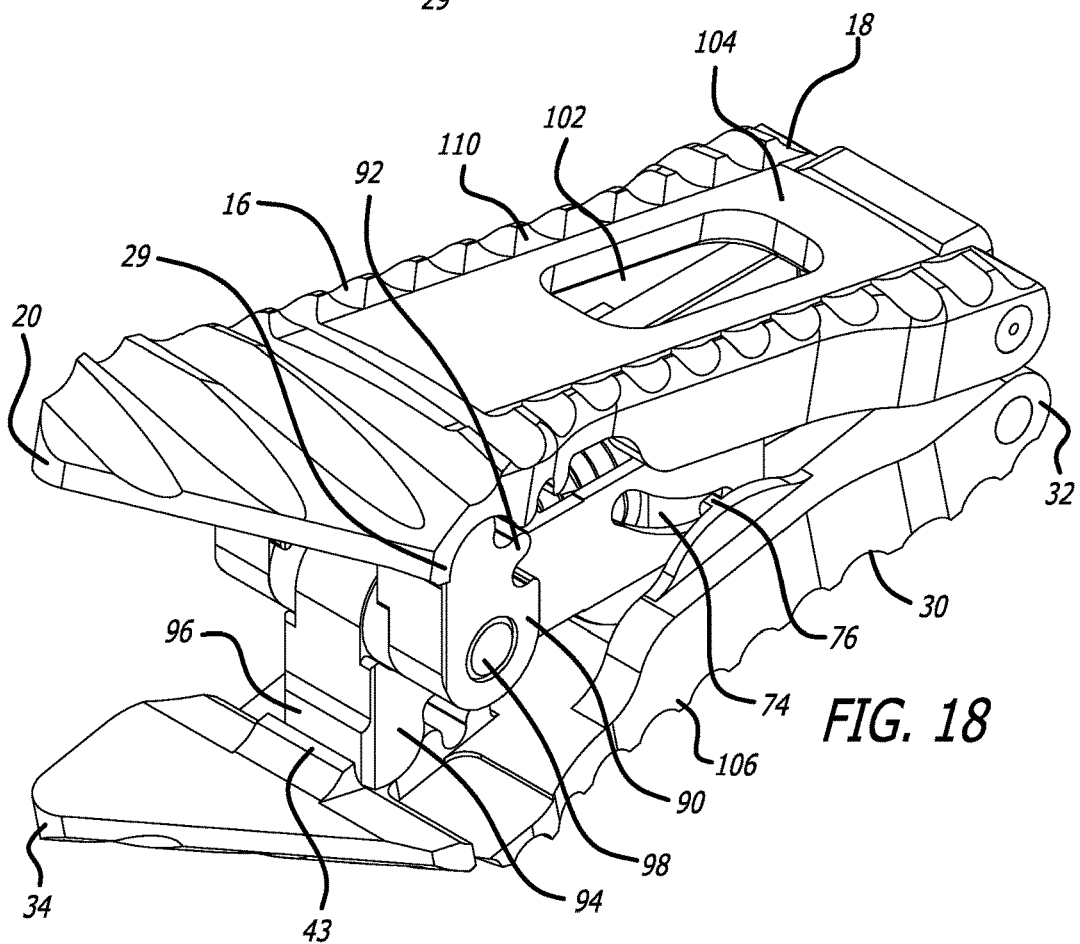
FIG. 18 is an upper perspective view of a geared cam expandable spinal implant in accordance with the invention, in a fully open position.

In one embodiment, as depicted in FIGS. 10-16, the spur gears 90 and 94 "walk" along the respective racks 26 and 40 in a multi-stage expansion movement, including the respective spur initially rolling along the respective rack, as depicted in FIGS. 10 and 11, and subsequently pivoting in a ball and socket fashion, as depicted in FIGS. 12 and 13. As depicted in FIGS. 14-16, the circumferences of the pitch diameters translate along each other as the gear is advanced.

This translation allows a higher angle of incidence at the starting point for the device as compared to a fixed-length link mechanism. The angle of incidence/mechanical advantage starts high and decreases as the gear is advanced, increasing as the gear advances further. The multi-stage expansion pattern allows a constant angle of attack of the gear with the rack.

Figure 1:
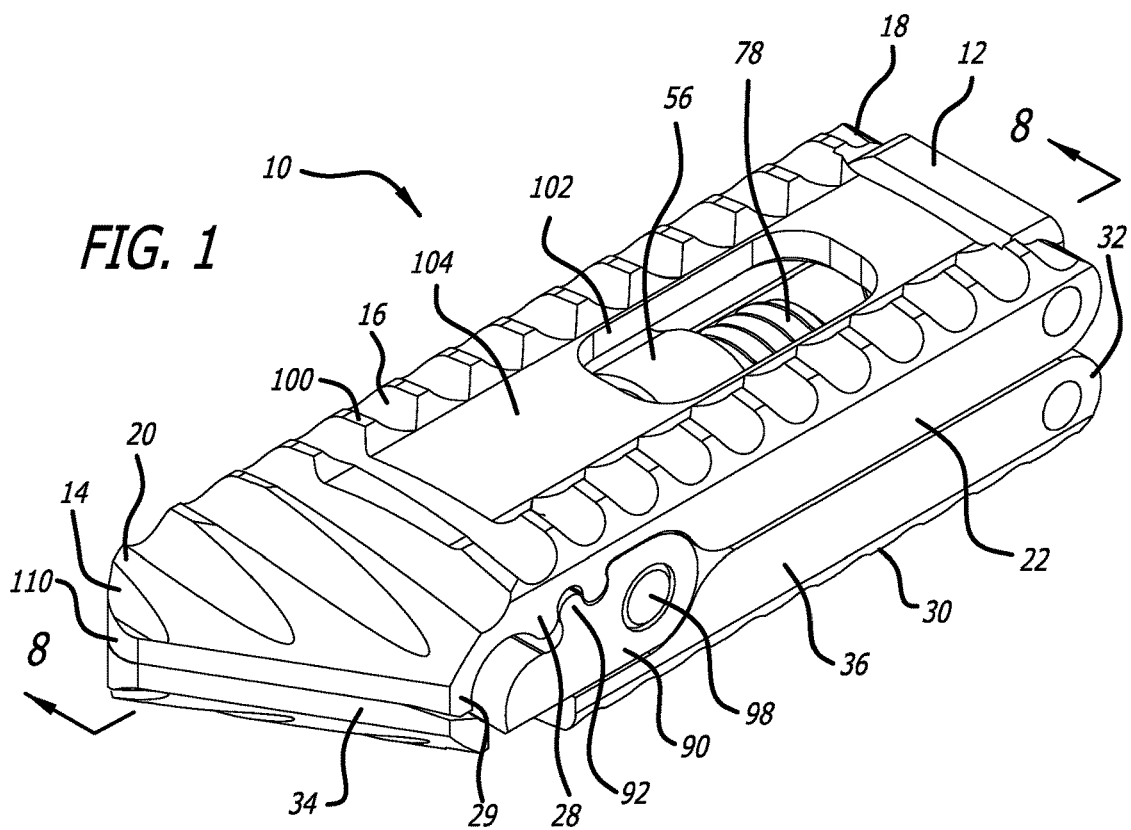
FIG. 1 is an upper perspective view of a geared cam expandable spinal implant in accordance with the invention, in a collapsed position.
Figure 2:
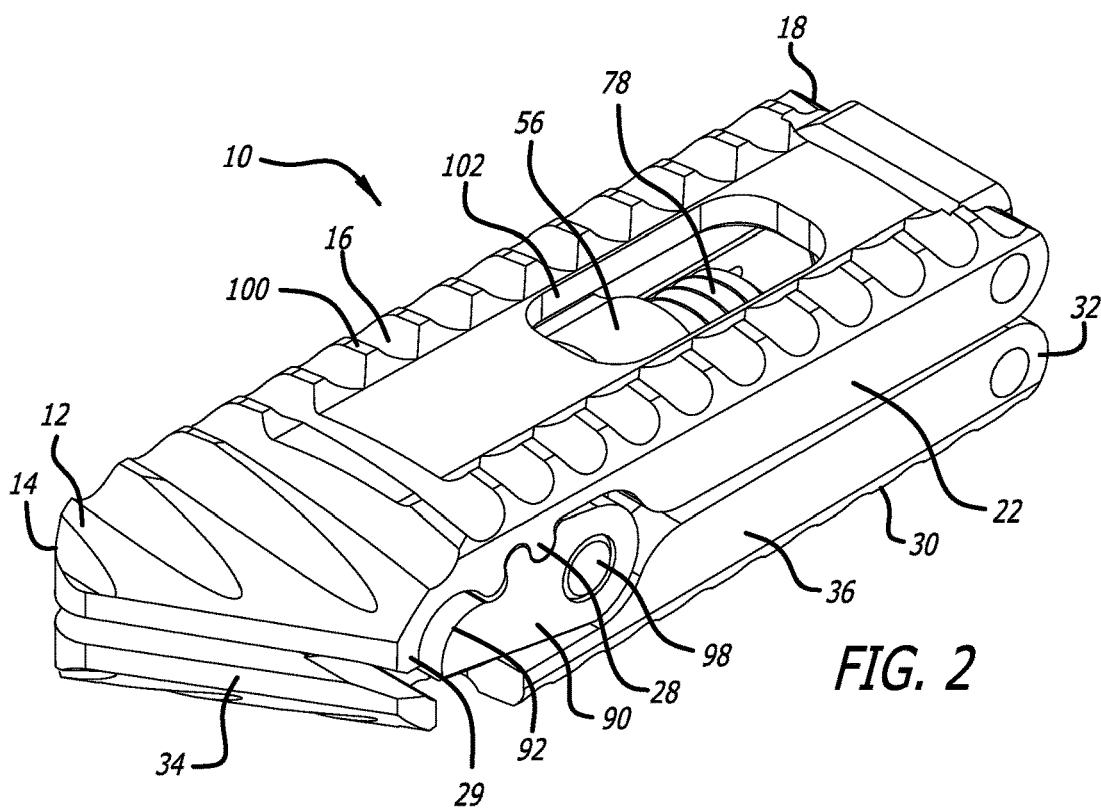
FIG. 2 is an upper perspective view of a geared cam expandable spinal implant in accordance with the invention, in a partially expanded position.

In one embodiment, as depicted in FIGS. 1 and 2, the upper endplate 16 includes projections 100, configured to engage a surface of the endplate of the upper vertebral body (not shown). The upper endplate 16 further includes an opening 102 defined therein, configured to allow bone growth from bone growth material loaded in the implant 10 to pass through the opening 102 and fuse with the upper vertebral body. The upper endplate 16 further includes a smooth surface 104, configured to distribute the vertebral body endplate loading. The smooth surfaces 104 can be configured along a majority of the length of the upper surface of the upper endplate 16, as depicted in FIGS. 1 and 2, or for only a portion of the length of the upper surface, to contact only the softer cancellous-like bone off the upper vertebral body endplate.

In one embodiment, as depicted in FIGS. 8 and 9, the lower endplate 30 includes projections 106 for engaging the endplate of the lower vertebral body (depicted in FIG. 45), and an opening 108 configured to allow bone growth from the bone graft material in the implant 10 to pass through the opening 108 and fuse with the lower vertebral body.

Figure 23:
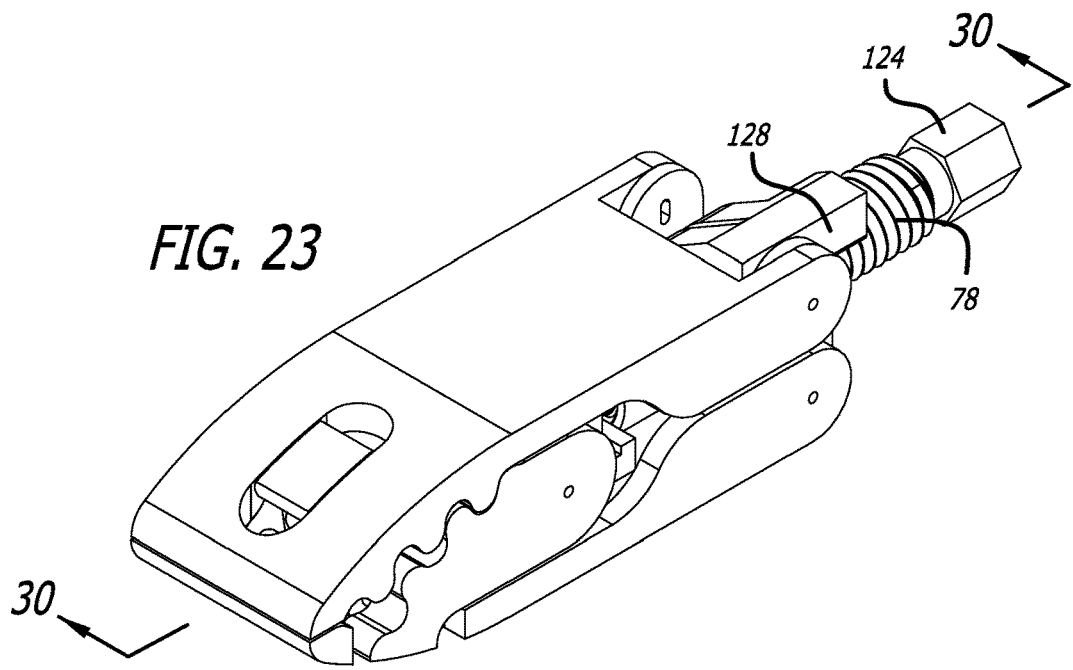
FIG. 23 is an upper perspective view of another embodiment of a geared cam expandable spinal implant in accordance with the invention, in a collapsed position.
Figure 24:
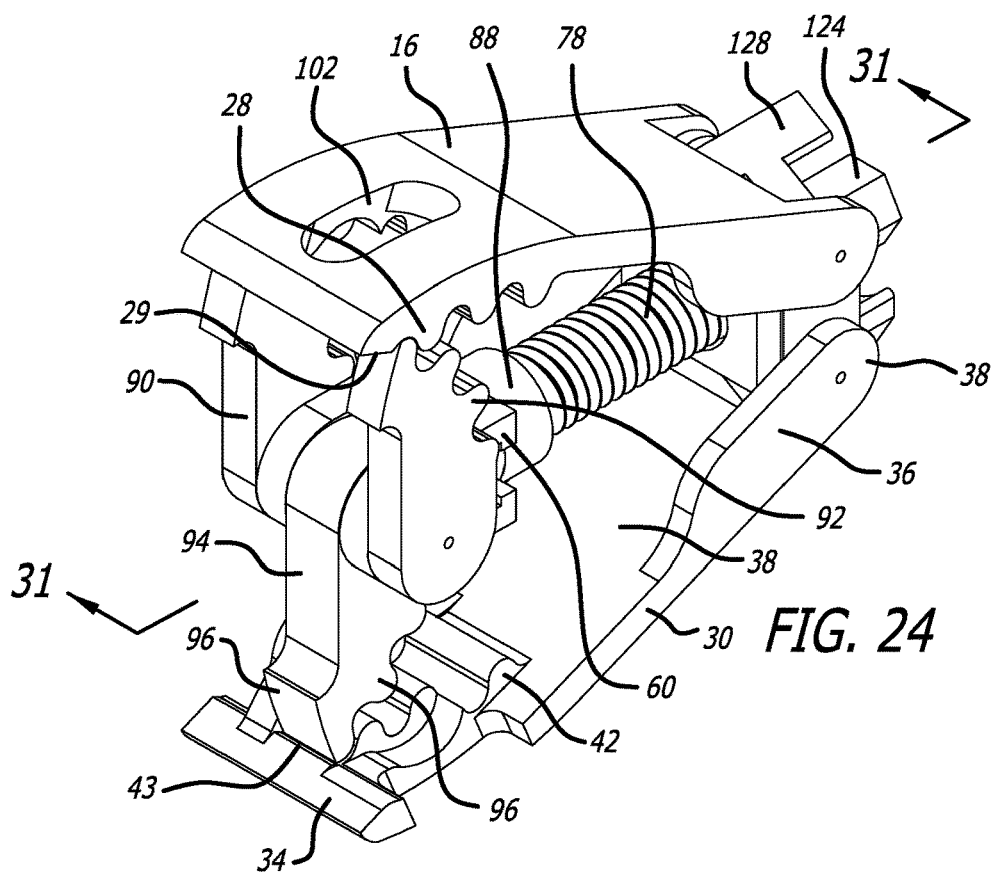
FIG. 24 is an upper perspective view of the embodiment of FIG. 23, in a fully expanded position.
Figure 25:
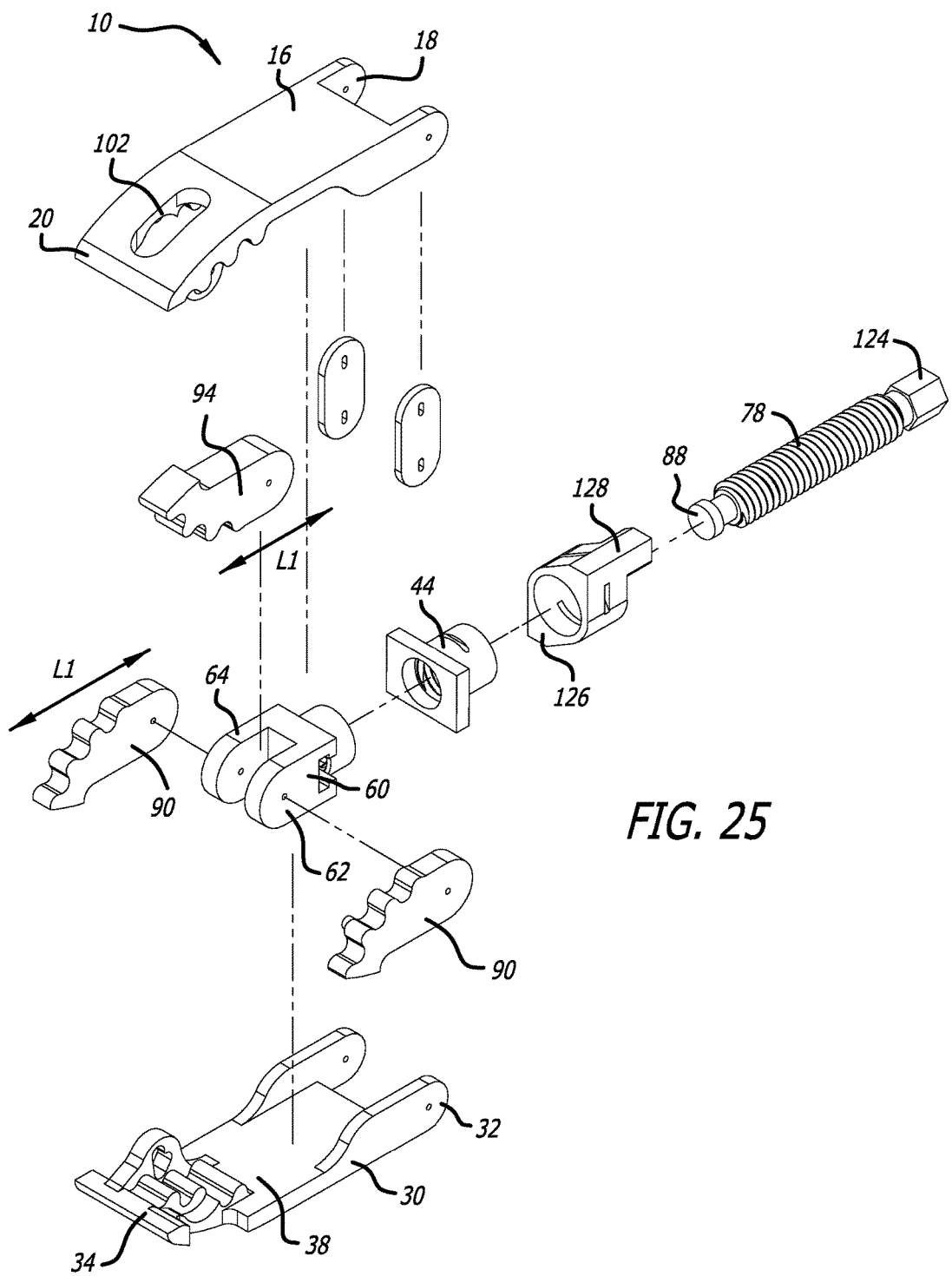
FIG. 25 is an exploded parts view of a geared cam expandable implant in accordance with the invention.
Figure 28:
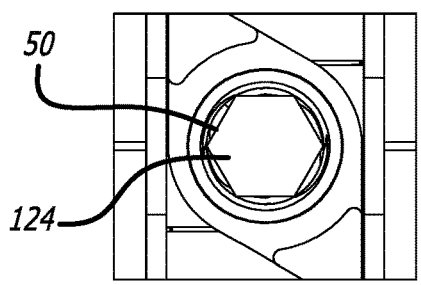
FIGS. 28 and 29 are rear views of a geared cam expandable spinal implant in accordance with the invention.
Figure 29:
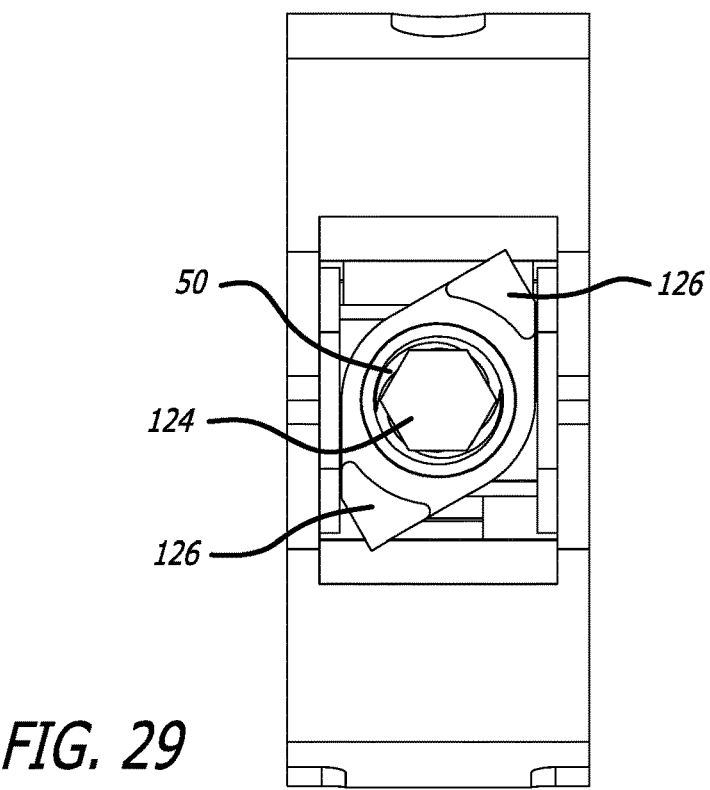
Figure 30:
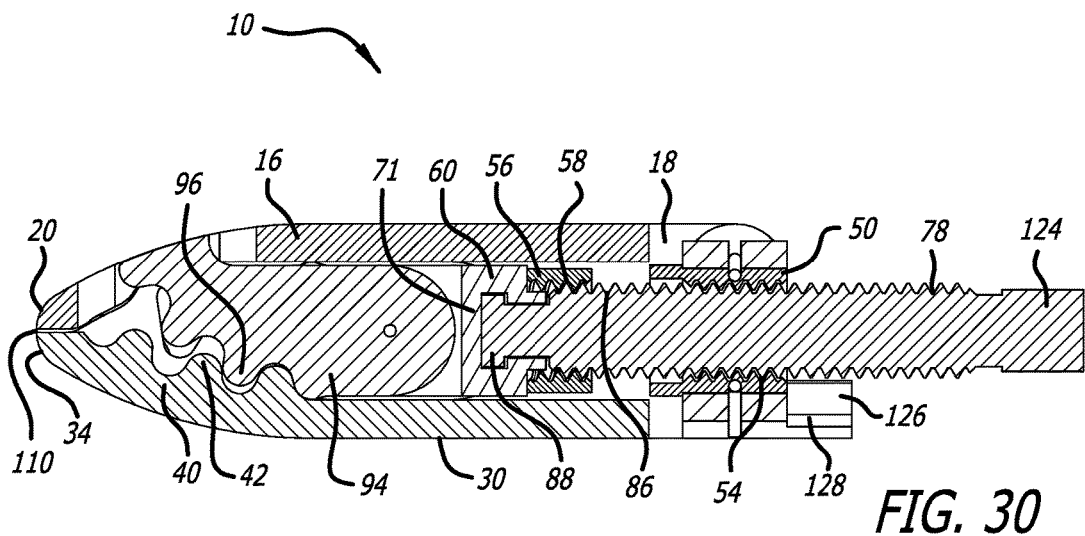
FIG. 30 is a side cross-sectional view of a geared cam expandable spinal implant in accordance with the invention in a collapsed position.
Figure 31:
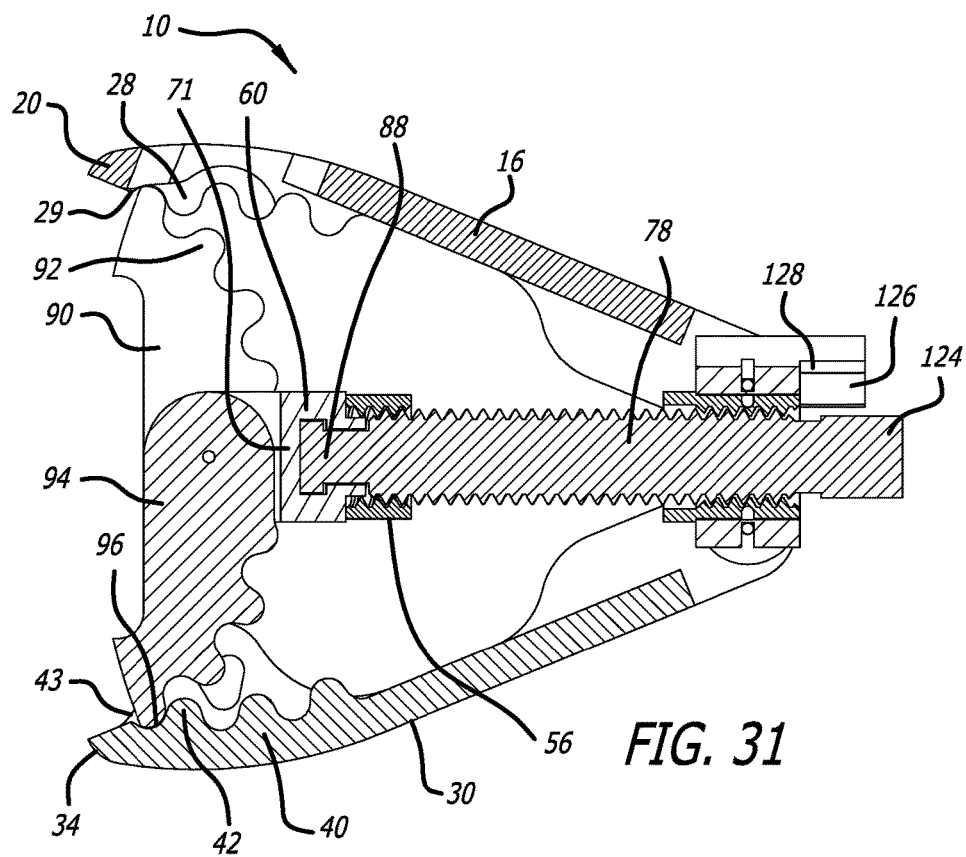
FIG. 31 is a side cross-sectional view of a geared cam expandable spinal implant in accordance with the invention in a fully expanded position.
Figure 45:
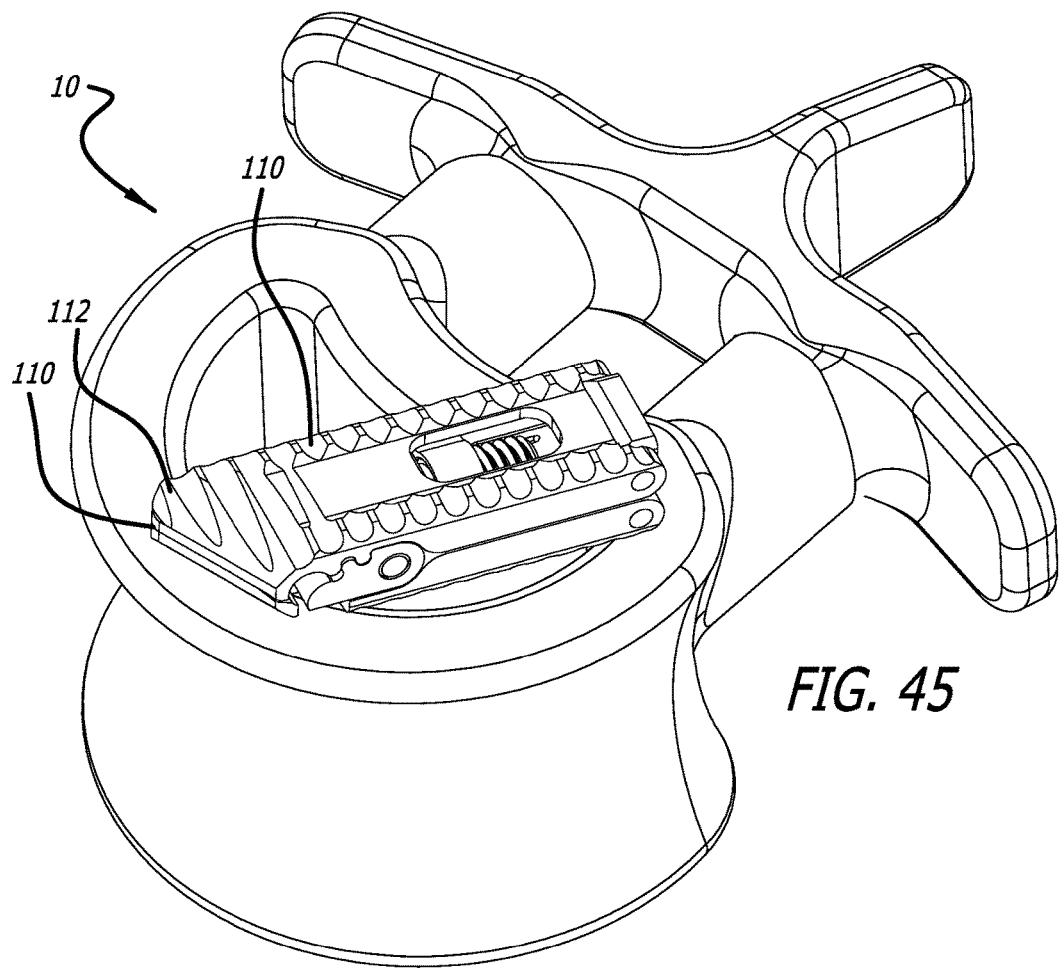
FIG. 45 is an upper perspective view of a geared cam expandable implant in accordance with the invention being supported by a lower vertebral body.

In one embodiment, the distal end 20 of the upper endplate 16, and the distal end 34 of the lower endplate 30 define a tip 110. The tip 110 can be beveled, as depicted in FIG. 45; flat, as depicted in FIGS. 23 and 24; or come to a central point, as depicted in FIG. 26.

In one embodiment, the tip 110 can include bone-engaging projections 112. In accordance with another embodiment, the tip 110 can have no projections. The bone-engaging projections 112 are configured to prevent implant migration as the implant 10 is expanding. The bone-engaging projections 112 may be perpendicular to the side surfaces 22 and 36, but generally follow the shape of the tip 110, or they could be parallel to the tip 110.

Figure 35:
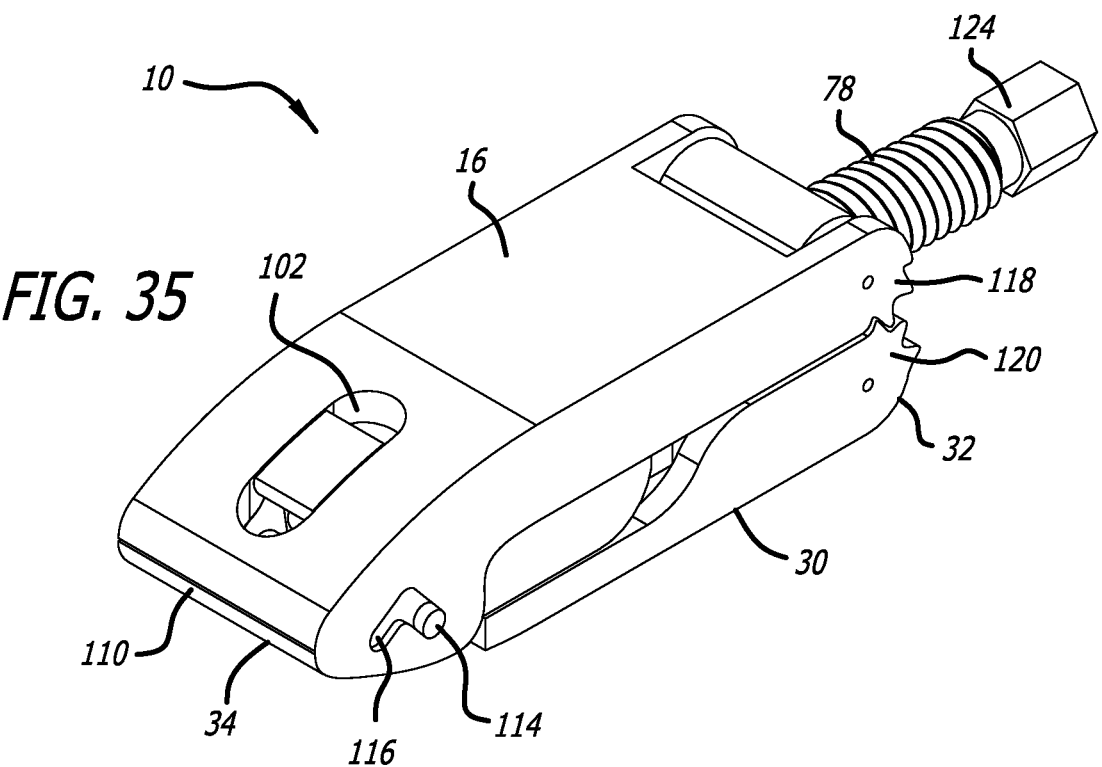
FIG. 35 is an upper perspective view of a geared cam expandable spinal implant in accordance with the invention in a collapsed position.
Figure 36:
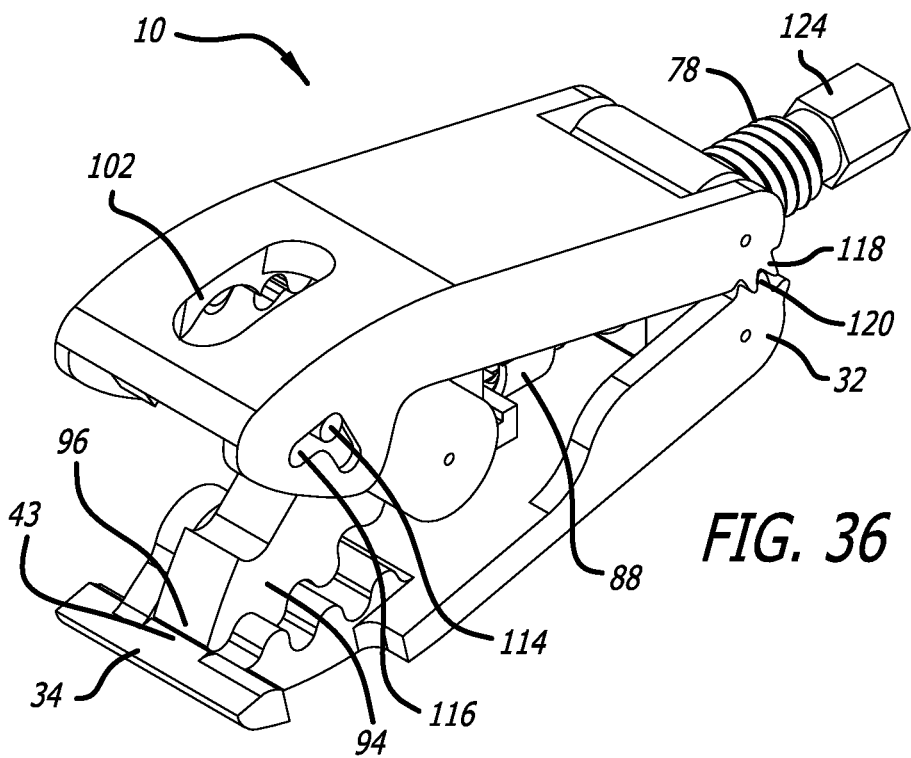
FIG. 36 is an upper perspective view of a geared cam expandable spinal implant in accordance with the invention in a fully expanded position.
Figure 37:
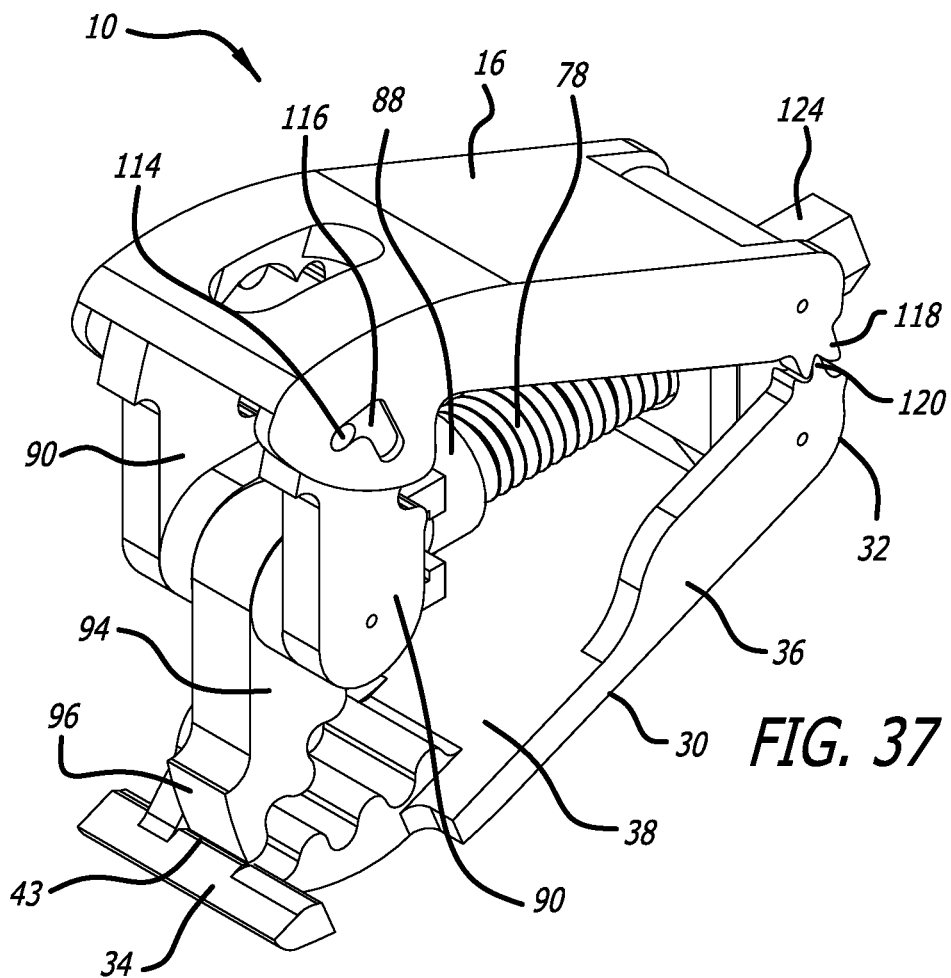
FIG. 37 is an upper perspective view of a geared cam expandable spinal implant in accordance with the invention in a fully expanded position.

In one embodiment as depicted in FIGS. 35 and 36, an engaging pin 114 extends from at least one spur gear 90 or 94, and is engaged in a slot 116 in a side of the upper endplate 16. Engagement of the engaging pin 114 in slot 116 assists in preventing the endplates 16 and 30 from decoupling during expansion of the implant 10.

In one embodiment, as depicted in FIGS. 35 and 36, an upper gear 118 is defined at the proximal end 18 of the upper endplate 16, in engagement with a lower gear 120 defined at the proximal end 32 of the lower endplate 30. Engagement of the upper and lower proximal gears 118 and 120, respectively, assists in preventing the endplates 16 and 30 from decoupling during expansion of the implant 10.

In one embodiment, an independent proximal expansion mechanism 122 is defined at the proximal end 12 of the implant 10. As depicted in FIGS. 28-31, 35, and 36, the proximal expansion mechanism 122 includes a proximal-end polygonal-shaped toggle 124, attached to the proximal end 80 of the rotating portion 78. A pair of proximal-end pivot pins 126 projects from the proximal-end toggle 124. In one embodiment, the toggle 124 can have one distraction position while in another embodiment, the toggle 124 can have progressive distraction positions. In one embodiment, the toggle 124 can be rotated, while in another embodiment, the toggle 124 can be translated. In the embodiment where the toggle 124 is rotated, the pivot pins 126 distract, using a cam-like action. In the embodiment where the toggle 124 is translated, the pivot pins 126 are distracted by sliding along proximal ramps 128.

In one embodiment, an insertion tool 130, depicted in FIGS. 38-44 and 46, includes a proximal end 132, and a distal end 134. An outer hollow cylindrical shaft 136 extends between the proximal end 132 and the distal end 134. An inner hollow cylindrical shaft 138 extends through the outer shaft 136. The inner shaft 138 has a proximal end 140 and a distal end 142.

Figure 38:
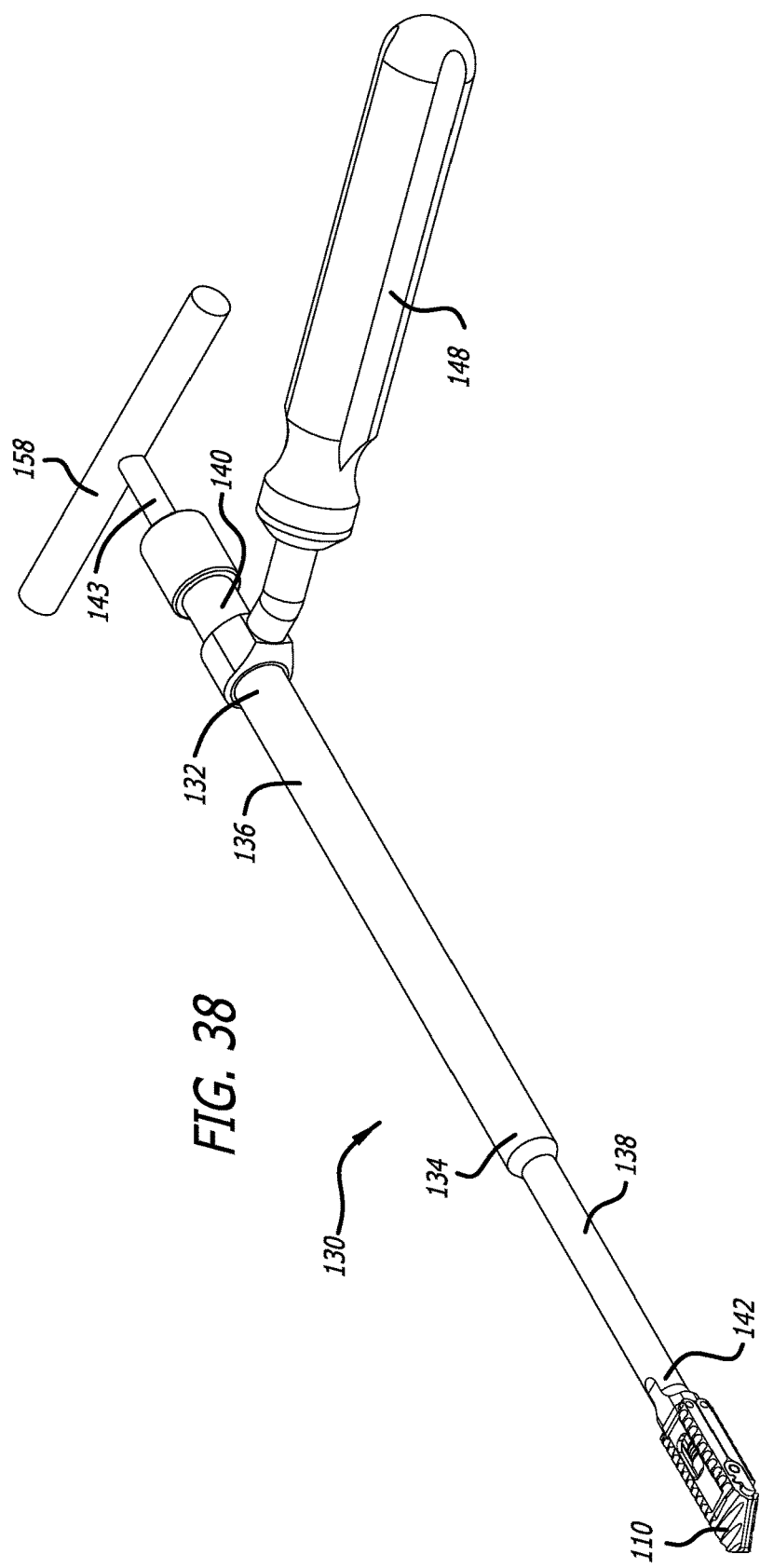
FIG. 38 is an upper perspective cross-sectional view of an implant insertion tool in accordance with the invention connected to a geared cam expandable spinal implant in accordance with the invention.

In one embodiment, as depicted in FIG. 38, a T-handle 158 is defined at the proximal end 140 of the inner shaft 138. The T-handle 158 attaches to an elongated driver 143, which extends through the inner shaft 138.

Figure 42:
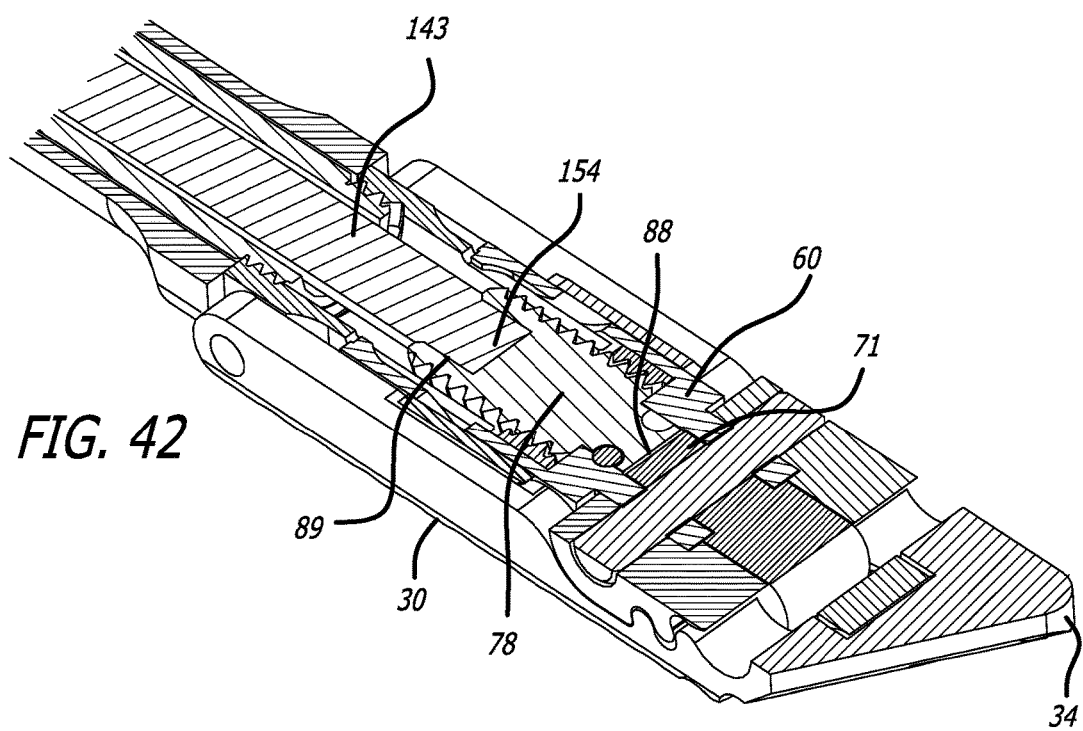
FIG. 42 is an upper perspective cross sectional view of a geared cam expandable implant in accordance with the invention being inserted into a disc space by an implant insertion tool in accordance with the invention.

In one embodiment, as depicted in FIGS. 42 and 43, the elongated driver 143 has a blunt distal end 154.

Figure 39:
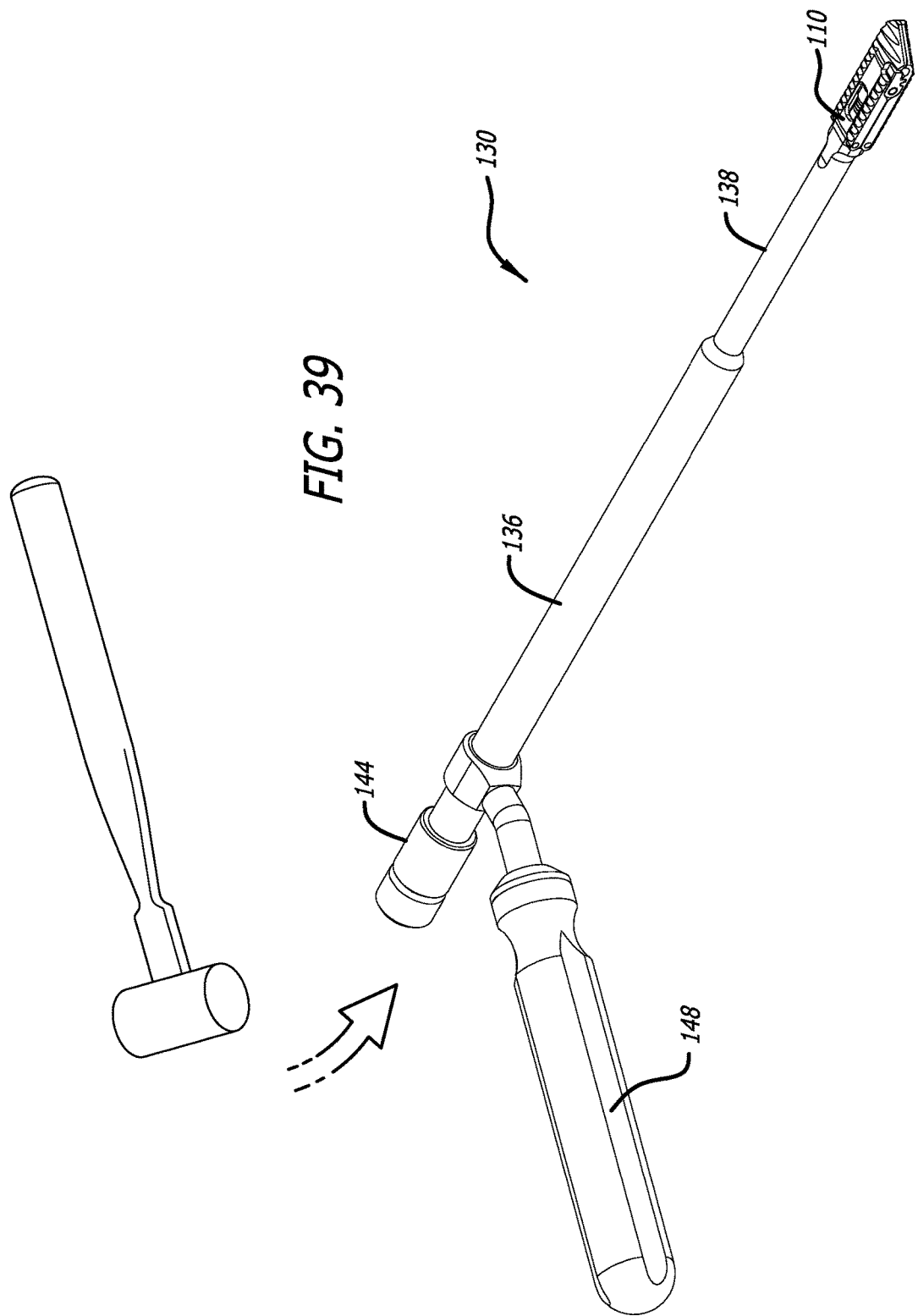
FIG. 39 is an upper perspective view of an implant insertion tool in accordance with the invention connected to a geared cam expandable spinal implant in accordance with the invention, depicting insertion of the implant into a disc space.

In one embodiment, as depicted in FIG. 39, a tap cap 144 is defined at the proximal end 140 of the inner shaft 138, attached to the driver 143.

Figure 40:
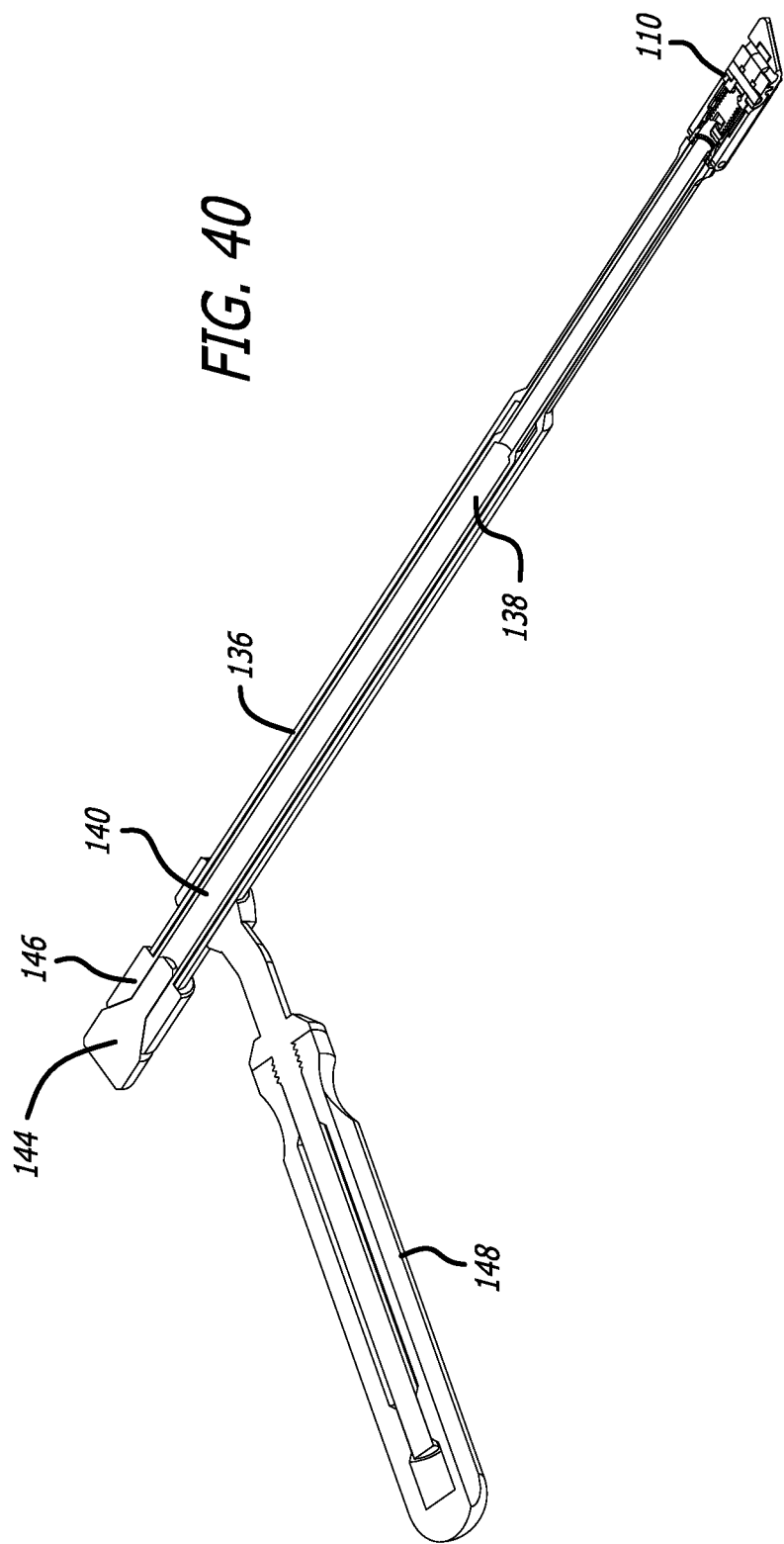
FIG. 40 is an upper perspective cross-sectional view of an implant insertion tool in accordance with the invention connected to a geared cam expandable spinal implant in accordance with the invention.
Figure 41:
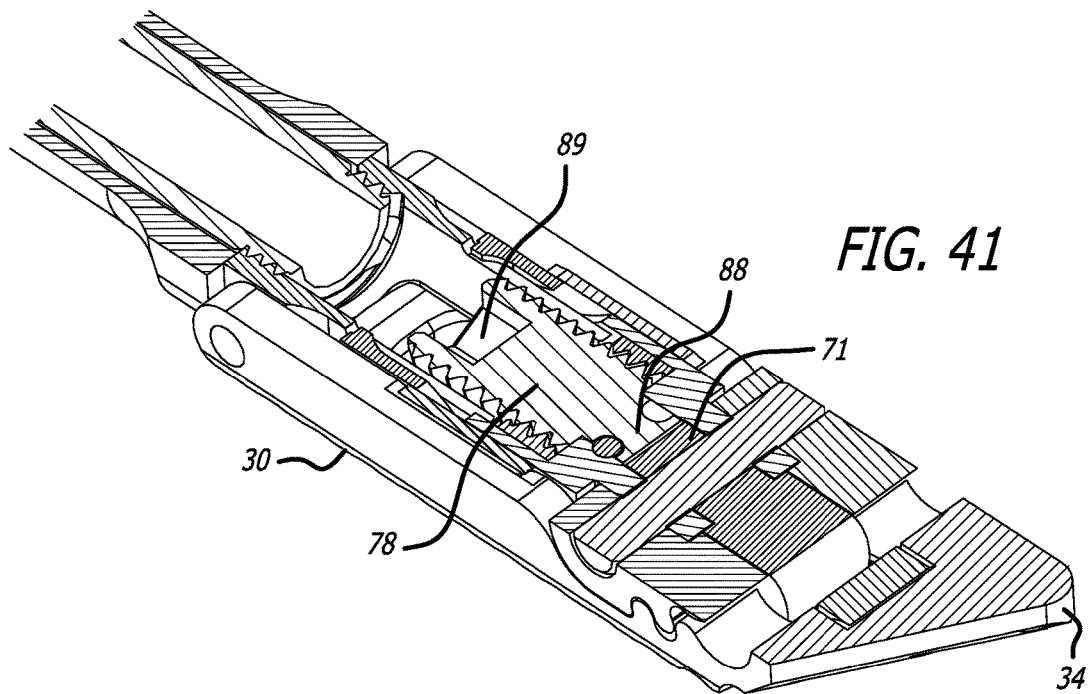
FIG. 41 is an upper perspective cross-sectional view of a geared cam expandable implant attached to an implant insertion tool in accordance with the invention.

In one embodiment, as depicted in FIG. 40, the tap cap 144 fits removably into a funnel 146 defined at the proximal end 140 of the inner shaft 138.

In one embodiment, a handle 148 is provided, gripping an outer surface of the outer shaft 136. Handle 148 is configured to be held by a surgeon while using the insertion tool 130.

Figure 46:
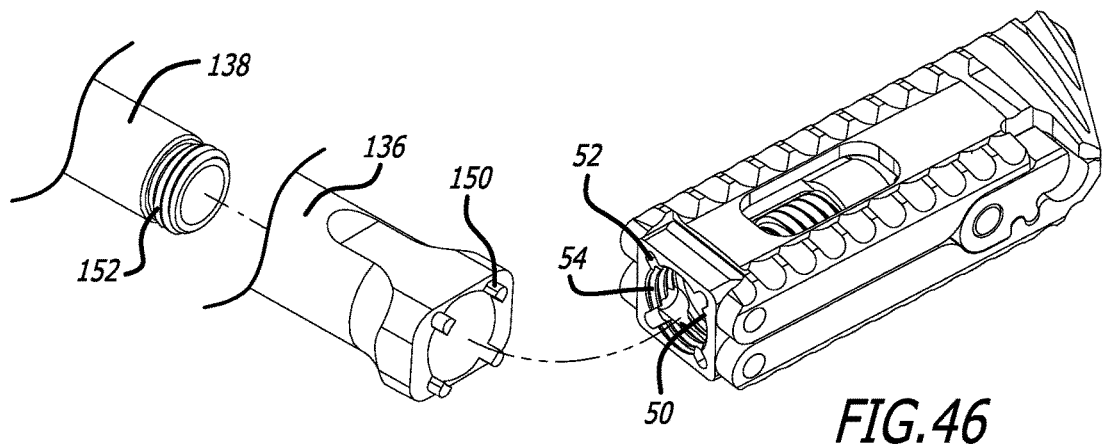
FIG. 46 is an upper perspective view depicting points of attachment between a geared cam expandable implant in accordance with the invention, and an implant insertion tool in accordance with the invention.

In one embodiment, as depicted in FIG. 46, the distal end 134 of the outer shaft 136 includes projecting fingers 150, configured to fit into the depressions 52, proximate the opening 50 in the proximal end 46 of the chassis portion 44.

In one embodiment, as depicted in FIGS. 40 and 46, the distal end 142 of the inner shaft 138 includes external threads 152, configured to engage the first set of inner threads 54 in the opening 50 of the chassis portion 44.

In one embodiment, as depicted in FIGS. 38, 39, and 42, moving the elongated driver 143, either by applying a force to the T-handle 158, or by applying a force to the tap cap 144, the elongated driver 143 is moved through the inner shaft 138, through the opening 50 in the proximal end 46 of the chassis portion 44, and through the chassis portion 44, until the blunt proximal end opening 89 in the rotating portion 78. Translation of the motion of the elongated driver 143 to the rotating portion 78 pushes the implant 10 into the disc space. Following removal of the elongated driver 143 from the implant 10 and the inner shaft 138, as depicted in FIG. 44, bone growth material can be inserted through the inner shaft 138 and into the implant 10.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

We claim:

1. An expandable spinal implant comprising:
 a proximal end and a distal end defining a mid-longitudinal axis therebetween, the expandable spinal implant being configured for insertion into a patient's disc space between an upper vertebral body and a lower vertebral body, and the expandable spinal implant being expandable between a collapsed position, a fully expanded position, and at least one partially expanded position between the collapsed position and the fully expanded position;
 an upper endplate, the upper endplate including a proximal end, a distal end, an outer surface, at least one side surface, and an inner surface, a portion of the inner surface including an upper rack portion, the upper rack portion including at least one downwardly-projecting tooth intermediate the proximal end and the distal end of the upper endplate, and at least one distal-most downwardly-projecting tooth proximate the distal end of the upper endplate;

a lower endplate, the lower endplate including a proximal end, a distal end, an outer surface, at least one side surface, and an inner surface, a portion of the inner surface including a lower rack portion, the lower rack portion including at least one upwardly-projecting tooth intermediate the proximal end and the distal end of the lower endplate, and at least one distal-most upwardly-projecting tooth proximate the distal end of the lower endplate, the proximal end of the lower endplate being pivotally connected to the proximal end of the upper endplate;

a chassis portion mounted within the implant between the upper endplate and the lower endplate, the chassis portion having a proximal end and a distal end, the proximal end having an opening defined therein, at least one depression defined therein proximate the opening, a first set of inner threads defined in the opening, and a second set of inner threads defined intermediate the proximal end and the distal end of the chassis portion;

a yoke movably mounted with respect to the chassis portion, the yoke having a proximal end and a distal end, and being defined by first and second substantially parallel spaced apart walls, each of the first and second spaced apart walls having a proximal end and a distal end;

a rotating portion rotatably mounted within the chassis portion, the rotating portion having an outer surface, a proximal end and a distal end, the proximal end having an opening defined therein, the distal end being positioned proximate the distal end of the yoke, and threads defined on at least a portion of the outer surface, the threads being engageable with the second set of inner threads in the chassis portion;

at least one first spur gear rotatably mounted to at least one of the distal ends of at least one of the first and second spaced apart walls of the yoke, the at least one first spur gear having at least one projecting first spur gear tooth configured to movably engage with the downwardly-depending teeth on the upper rack portion; and at least one second spur gear rotatably mounted to at least one of the distal ends of at least one of the first and second spaced apart walls of the yoke, the at least one second spur gear having at least one projecting second spur gear tooth configured to engage with the upwardly-projecting teeth on the lower rack portion;

wherein the rotating portion is further configured to translate rotational motion thereof to linear motion of the yoke, the yoke translating the linear motion to rotational motion of at least the at least one first spur gear, thereby rotating the at least one first spur gear with respect to the yoke; and wherein the rotation of the at least one first spur gear with respect to the yoke defines a first linear walking motion of the at least one projecting first spur gear tooth along the downwardly-depending upper rack gear teeth toward the distal end of the implant, thereby pivoting the upper endplate to the at least one partially expanded position.

2. The expandable spinal implant of claim 1, wherein the opening in the proximal end of the rotating portion is configured to receive a distal end of a cam expansion tool.

3. The expandable spinal implant of claim 1, wherein at least one of the upper endplate and the lower endplate includes at least one projection projecting from the outer surface thereof, the at least one projection configured to engage a corresponding endplate of a respective one of the upper vertebral body and the lower vertebral body.

4. The expandable spinal implant of claim 1, wherein the yoke further includes at least one side surface, the at least one side surface having a track defined therein, the track being configured to receive therein a peg projecting from the at least one side surface of one of the lower endplate and the upper endplate, thereby preventing disengagement of the upper endplate from the lower endplate.

5. The expandable spinal implant of claim 1, wherein the rotation of the rotating portion further translates motion to at least the at least one second spur gear to rotate the at least one second spur gear with respect to the yoke, the rotation of the at least the at least one second spur gear with respect to the yoke defining a second linear walking motion of the at least one projecting second spur gear tooth along the upwardly-projecting lower rack gear teeth toward the distal end of the implant, pivoting the lower endplate to the at least one partially expanded position.

6. The expandable spinal implant of claim 5, wherein at least the lower rack portion includes a distal-most upwardly-projecting lower rack gear tooth being configured to interact with the at least one second spur gear top stop the second linear walking motion.

7. The expandable spinal implant of claim 1, wherein the distal end of the upper endplate and the distal end of the lower endplate cooperate to form a tip.

8. The expandable spinal implant of claim 7, wherein the tip defines one of a substantially perpendicular angle with respect to the mid-longitudinal axis and a substantially oblique angle with respect to the longitudinal axis.

9. The expandable spinal implant of claim 7, wherein the distal end of the upper endplate and the distal end of the lower endplate cooperate to define one of a beveled edge, a pointed edge, and a planar edge.

10. The expandable spinal implant of claim 7, wherein the tip includes at least one projection configured for engagement with a corresponding endplate of the respective upper vertebral body and lower vertebral body.

11. The expandable spinal implant of claim 1, wherein the rotating portion is generally cylindrical.

12. The expandable spinal implant of claim 1, wherein at least one of the upper endplate and the lower endplate includes an aperture defined in the outer surface thereof, the aperture configured to allow bone growth therethrough.

13. The expandable spinal implant of claim 1, wherein at least the upper rack portion includes a distal-most downwardly-depending upper rack gear tooth being configured to interact with the at least one first spur gear to stop the first linear walking motion.

14. The expandable spinal implant of claim 1, wherein the rotating portion comprises a threaded screw.

15. The expandable spinal implant of claim 1, wherein the rotating portion includes a substantially T-shaped projection defined at the distal end thereof, the substantially T-shaped projection adapted to contact the yoke.

16. The expandable spinal implant of claim 1, wherein the chassis portion further includes an arcuate portion intermediate the proximal end and the distal end.

17. The expandable spinal implant of claim 1, wherein the distal end of the yoke further comprises a distal end crosspiece, substantially transverse to the longitudinal axis, connecting the distal ends of the first and second walls of the yoke.

18. The expandable spinal implant of claim 1, wherein at least one of the at least one first spur gear and the at least one second spur gear has a length, the amount of implant expansion in the fully expanded position being related to the length.

19. A kit for inserting an expandable spinal implant into a patient's disc space between an upper vertebral body and a lower vertebral body, the kit comprising:
   the implant, the implant comprising:
      a proximal end and a distal end defining a mid-longitudinal axis therebetween, the expandable spinal implant being expandable between a collapsed position, a fully expanded position, and at least one partially expanded position between the collapsed position and the fully expanded position;
      an upper endplate, the upper endplate including a proximal end, a distal end, an outer surface, at least one side surface, and an inner surface, a portion of the inner surface including an upper rack portion, the upper rack portion including at least one downwardly-projecting tooth intermediate the proximal end and the distal end of the upper endplate, and at least one distal-most downwardly-projecting tooth proximate the distal end of the upper endplate;
      a lower endplate, the lower endplate including a proximal end, a distal end, an outer surface, at least one side surface, and an inner surface, a portion of the inner surface including a lower rack portion, the lower rack portion including at least one upwardly-projecting tooth intermediate the proximal end and the distal end of the lower endplate, and at least one distal-most upwardly-projecting tooth proximate the distal end of the lower endplate, the proximal end of the lower endplate being pivotally connected to the proximal end of the upper endplate;
      a chassis portion mounted within the implant between the upper endplate and the lower endplate, the chassis portion having a proximal end and a distal end, the proximal end having an opening defined therein, at least one depression defined therein proximate the opening, a first set of inner threads defined in the opening, and a second set of inner threads defined intermediate the proximal end and the distal end of the chassis portion;
      a yoke movably mounted with respect to the chassis portion, the yoke having a proximal end and a distal end, and being defined by first and second substantially parallel spaced apart walls, each of the first and second spaced apart walls having a proximal end and a distal end;
      a rotating portion rotatably mounted within the chassis portion, the rotating portion having an outer surface, a proximal end, and a distal end, the proximal end having an opening defined therein, the distal end being positioned proximate the distal end of the yoke, and threads defined on at least a portion of the outer surface, the threads being engageable with the second set of inner threads in the chassis portion;
      at least one first spur gear rotatably mounted to at least one of the distal ends of at least one of the first and second spaced apart walls of the yoke, the at least one first spur gear having at least one projecting first spur gear tooth configured to movably engage with the downwardly-depending teeth on the upper rack portion; and
      at least one second spur gear rotatably mounted to at least one of the distal ends of at least one of the first and second spaced apart walls of the yoke, the at least one second spur gear having at least one projecting second spur gear tooth configured to engage with the upwardly-projecting teeth on the lower rack portion;
      wherein the rotating portion is further configured to translate rotational motion thereof to linear motion of the yoke, the yoke translating the linear motion to rotational motion of at least the at least one first spur gear, thereby rotating the at least one first spur gear with respect to the yoke; and
      wherein the rotation of at least the at least one first spur gear with respect to the yoke defines a first linear walking motion of the at least one projecting first spur gear tooth along the downwardly-depending upper rack gear teeth toward the distal end of the implant, thereby pivoting the upper endplate to the at least one partially expanded position; and an insertion tool attachable to the proximal end of the implant.

20. The kit of claim 19, wherein the insertion tool includes a proximal end and a distal end, and comprises:
   at least one outer hollow substantially cylindrical shaft, the at least one outer shaft having a proximal end and a distal end, the distal end including at least one projecting finger portion, the at least one projecting finger portion being configured to engage the at least one depression defined in the posterior wall of the chassis portion;
   an inner substantially cylindrical shaft configured to pass through the at least one outer shaft, the inner shaft having a proximal end and a distal end, the distal end including a set of external threads defined on an outer peripheral surface thereof, the set of external threads being configured to engage the first set of inner threads in the chassis portion.

21. The kit of claim 20, wherein the proximal end of the inner shaft further comprises a funnel portion defined at the proximal end configured to insert bone graft material into the outer shaft.

22. The kit of claim 21, wherein the outer shaft is adapted to transfer the bone graft material from the funnel portion to the chassis portion of the implant.

23. The kit of claim 20, further comprising an elongated driver rod extending through the inner shaft.

* * * * *